US008835384B2

(12) United States Patent
Terzic et al.

(10) Patent No.: US 8,835,384 B2
(45) Date of Patent: Sep. 16, 2014

(54) COMPOSITIONS AND METHODS FOR OBTAINING CELLS TO TREAT HEART TISSUE

(75) Inventors: Andre Terzic, Rochester, MN (US); Atta Behfar, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 15 days.

(21) Appl. No.: 12/994,626

(22) PCT Filed: May 20, 2009

(86) PCT No.: PCT/US2009/044714
§ 371 (c)(1),
(2), (4) Date: Jan. 11, 2011

(87) PCT Pub. No.: WO2009/151907
PCT Pub. Date: Dec. 17, 2009

(65) Prior Publication Data
US 2011/0117065 A1      May 19, 2011

Related U.S. Application Data

(63) Continuation-in-part of application No. PCT/US2008/064895, filed on May 27, 2008.

(51) Int. Cl.
*A61K 38/18* (2006.01)
*A61K 38/36* (2006.01)

(52) U.S. Cl.
USPC ............ 514/8.8; 514/8.9; 514/14.7; 514/16.5

(58) Field of Classification Search
None
See application file for complete search history.

(56) References Cited

U.S. PATENT DOCUMENTS

| | | | |
|---|---|---|---|
| 5,839,438 | A | 11/1998 | Graettinger et al. |
| 6,833,269 | B2 | 12/2004 | Carpenter |
| 7,425,448 | B2 | 9/2008 | Xu |
| 7,452,718 | B2 | 11/2008 | Gold et al. |
| 7,732,199 | B2 | 6/2010 | Xu et al. |
| 8,071,380 | B2 | 12/2011 | Cossu et al. |
| 8,158,421 | B2 | 4/2012 | Passier et al. |
| 8,173,118 | B2 | 5/2012 | Terzic et al. |
| 2002/0039557 | A1 | 4/2002 | White |
| 2002/0061837 | A1 | 5/2002 | Lough et al. |
| 2003/0224345 | A1 | 12/2003 | West et al. |
| 2003/0229908 | A1 | 12/2003 | Cibelli et al. |
| 2005/0164382 | A1 | 7/2005 | Xu |
| 2007/0274970 | A1 | 11/2007 | Gordon et al. |
| 2008/0019944 | A1* | 1/2008 | Terzic et al. ................. 424/93.1 |
| 2008/0057028 | A1 | 3/2008 | Alitalo et al. |
| 2010/0009399 | A1 | 1/2010 | Sartipy et al. |
| 2010/0166714 | A1 | 7/2010 | Chien et al. |
| 2010/0189697 | A1 | 7/2010 | Terzic et al. |
| 2012/0100533 | A1 | 4/2012 | Terzic et al. |
| 2012/0178164 | A1 | 7/2012 | Terzic et al. |

FOREIGN PATENT DOCUMENTS

| | | |
|---|---|---|
| JP | 2002-511094 | 4/2002 |
| JP | 2007-517831 | 7/2007 |
| JP | 2007-537692 | 12/2007 |
| WO | 2005/038454 | 4/2005 |
| WO | 2005/090558 | 9/2005 |
| WO | 2006/015127 | 2/2006 |
| WO | WO2006/032054 | 3/2006 |
| WO | WO2006/081190 | 8/2006 |
| WO | WO 2007/012009 | 1/2007 |
| WO | WO2008/109839 | 9/2008 |
| WO | WO2009/145761 | 12/2009 |
| WO | WO2010/133686 | 11/2010 |
| WO | WO2010/135555 | 11/2010 |

OTHER PUBLICATIONS

Lev et al. (Ann. N.Y. Acad. Sci. 1047: 50-65, 2005).*
Ma et al. Cardiovascular Research 71: 158-169, 2006.*
Aicher et al., "Essential role of endothelial nitric oxide synthase for mobilization of stem and progenitor cells," *Nature Medicine*, 2003, 9: 1370-1376.
Andree et al., "BMP-2 induces ectopic expression of cardiac lineage markers and interferes with somite formation in chicken embryos," *Mech. Dev.*, 1998, 70(1-2):119-131.
Anversa and Nadal-Ginard, "Myocyte renewal and ventricular remodelling," *Nature*, 2002, 415:240-243.
Arrell et al., "Proteomic analysis of pharmacologically perconditioned cardiomyocytes reveals novel phosphorylation of myosin light chain 1," *Circulation Research*, 2001, 89: 480-487.
Askari et al., "Effect of stromal-cell-derived factor 1 on stem-cell homing and tissue regeneration in ischaemic cardiomyopathy," *Mechanisms of Disease*, 2003, 362: 697-703.
Baddoo et al., "Characterization of Mesenchymal Stem Cells Isolated from Murine Bone Marrow by Negative Selection," *Journal of Cellular Biochemistry*, 2003, 89: 1235-1249.
Behfar and Terzic, "Derivation of a cardiopoietic population from human mesenchymal stem cells yields cardiac progeny," *Nat. Clin. Pract. Cardiovasc. Med.*, 2006, 3(Suppl 1):S78-S82.
Behfar et al., "Administration of allogenic stem cells dosed to secure cardiogenesis and sustained infarct repair," *Ann. NY Acad. Sci.*, 2005, 1049:189-198.
Behfar et al., "Stem cell differentiation requires a paracrine pathway in the heart," *FASEB J.*, 2002, 16:1558-1556.
Behfar et al., "Cardiopoietic programming of embryonic stem cells for tumor-free heart repair," *J. Exp. Med.*, 2007, 204(2):405-420.
Behfar et al., "Newly Identified Cardiopoietic Stem Cell Population Recruited by TNF-α from Pluripotent Embryonic Cells," *Circulation*, 2004, 110(17):III-302, Abstract No. 1444.
Beltrami et al., "Evidence that human cardiac myocytes divide after myocardial infarction," *N. Engl. J. Med.*, 2001, 344:1750-1757.
Beltrami et al., "Adult cardiac stem cells are multipotent and support myocardial regeneration," *Cell*, 2003, 114:763-776.
Boheler et al., "Differentiation of pluripotent embryonic stem cells into cardiomyocytes," *Circ. Res.*, 2002, 91:189-201.

(Continued)

*Primary Examiner* — Christine J Saoud
(74) *Attorney, Agent, or Firm* — Fish & Richardson P.C.

(57) ABSTRACT

This document relates to compositions containing cardiogenic factors, to methods to obtain cells by culturing initial cells in the presence of such factors; and methods of administering the obtained cells to heart tissue.

5 Claims, 13 Drawing Sheets

(56) References Cited

OTHER PUBLICATIONS

Bondue et al., "Mesp1 acts as a master regulator of multipotent cardiovascular progenitor specification," *Cell Stem Cell*, 2008, 3(1): 69-84.
Britten et al., "Infarct remodeling after intracoronary progenitor cell treatment in patients with acute myocardial infarction (TOPCARE-AMI): Mechanistic insights from serial contrast-enhanced magnetic resonance imaging," *Circulation*, 2003, pp. 2212-2218.
Caplice et al., "Cell therapy for cardiovascular disease: what cells, what diseases and for whom?" *Nat. Clin. Pract. Cardiovasc. Med.*, 2005, 2:37-43.
Chien et al., ES Cells to the Rescue, *Science*, 2004, 306:239-240.
Daniels et al., "Imatinib mesylate inhibits the profibrogenic activity of TGF-β and prevents bleomycin mediated lung fibrosis," *J Clin invest*, 2004, 114: 1308-1316.
Dawn and Bolli, "Bone marrow cells for cardiac regeneration: the quest for the protagonist continues," *Cardiovasc. Res.*, 2005, 65(2):293-295.
Dawn et al., "Cardiac stem cells delivered intravascularly traverse the vessel barrier, regenerate infracted myocardium, and improve cardiac function," *PNAS*, 2005, 102(10): 3766-3771.
Dimmeler et al., "Unchain my heart: the scientific foundations of cardiac repair," *J. Clin. Invest.*, 2005, 115(3):572-583.
Drukker et al., "Characterization of the expression of MHC proteins in human embryonic stem cells," *PNAS*, 2002, 99(15): 9864-9869.
Edgeworth et al., "Ionomycin-regulated phosphorylation of the myeloid calcium-binding protein p14," *Nature*, 1989, 342:189-192.
Erdo et al., "Host-dependent tumorigenesis of embryonic stem cell transplanation in experimental stroke," J. Cereb. Blood Flow Metab., 2003, 23:780-785.
Fernández-Avilés et al., "Experimental and Clinical Regenerative Capability of Human Bone Marrow Cells After Myocardial Infarction," *Circ. Res.*, 2004, 95:742-748.
Fijnvandraat et al., "Cardiomyocytes purified from differentiated embryonic stem cells exhibit characteristics of early chamber myocardium," *J. Mol. Cell. Cardiol.*, 2003, 35(12):1461-1472.
Foley and Mercola, *Trends Cardiovasc. Med.*, 2004, 14:121-125.
Fraidenraich et al., "Rescue of Cardiac Defects in id Knockout Embryos by Injection of Embryonic Stem Cells," *Science*, 2004, 306:247-252.
Frandrich et al., "Preimplantation-stage stem cells induce long-term allogeneic graft acceptance without supplementary host conditioning," *Nature Medicine*, 2002, 8(2): 171-178.
Fukuda, "Development of Regenerative Cardiomyocytes from Mesenchymal Stem Cells for Cardiovascular Tissue Engineering," *Artificial Organs*, 2001, 25(3):187-193.
Fukuda, "Molecular characterization of regenerated cardiomyocytes derived from adult mesenchymal stem cells," *Congenital Anomalies*, 2002, 42:1-9.
Gepstein, "Derivation and potential applications of human embryonic stem cells," *Circ. Res.*, 2002, 91:866-876.
Gharandaghi et al., "Mass spectrometric identification of proteins from silver-stained polyacrylamide gel: A method for the removal of silver ions to enhance sensitiviry," *Electrophoresis*,1999, 20: 601-605.
Ghosh et al., "Physical interaction between TBX5 and MEF2C is required for early heart development," *Molecular and Cellular Biology*, 2009, 29(8): 2205-2218.
Gnecchi et al., "Paracrine action accounts for marked protection of ischemic heart by Akt-modified mesenchymal stem cells," *Nat. Med.*, 2005, 11(4):367-368.
He et al., "Human embryonic stem cells develop into multiple types of cardiac myocytes: Action potential characterization," *Circ. Res.*, 2003, 93:32-39.
Hodgson et al., "Cellular remodeling in heart failure disrupts $K_{ATP}$ channel-dependent stress tolerance," *EMBO J.*, 2003, 22(8):1732-1742.
Hodgson et al., "Stable benefit of embryonic stem cell therapy in myocardial infarction," *Am. J.Physiol. Heart Circ. Physiol.*, 2004, 287:H471-H479.
Itescu et al., "New directions in strategies using cell therapy for heart disease," *J. Mol. Med.*, 2003, 82: 288-296.
Jiang et al., "Common Role for Each of the cGATA-4/5/6 Genes in the Regulation of Cardiac Morphogenesis," *Dev. Genet.*, 1998, 22:263-277.
Jiang et al., "Pluripotency of mesenchymal stem cells derived from adult marrow," *Nature*, 2002, 418:41-49.
Kane et al., "ATP-Sensitive K+ challel knockout compromises the metabolic benefit of exercise training, resulting in cardiac deficits," *Diabetes*, 2004, 53: 169-175.
Kehat et al., "Electromechanical integration of cardiomyocytes derived from human embryonic stem cells," *Nat. Biotechnol.*, 2004, 22:1282-1289.
Koh et al., "Co-culture of human CD34+ cells with mesenchymal stem cells increases the survival of CD34+ cells against the 5-aza-deoxycytidine- or trichostatin A-induced cell death," *Biochem. Biophys. Res. Commun.*, 2005, 329:1039-1045.
Kucia et al., "Cells Expressing Early Cardiac Markers Reside in the Bone Marrow and Are Mobilized Into the Peripheral Blood After Myocardial Infarction," *Circ. Res.*, 2004, 95:1191-1199.
Kwon et al., "An essential role of N-terminal arginylation in cardiovascular development," *Science*, 2002, 297:96-99.
Laugwitz et al., "Postnatal isl1+ cardioblasts enter fully differentiated cardiomyocyte lineages," *Nature*, 2005, 433:647-653.
Levenberg et al., "Endothelial cells derived from human embryonic stem cells," *PNAS*, 2002, 99: 4391-4396.
Lila et al., "Human leukocyte antigen-G expression after heart transplantation is assocaited with a reduced indicence of rejection," *Circulation*, 2002, 105: 1949-1954.
Lin et al., "Control of mouse cardiac morphogenesis and myogenesis by tanscription factor MEF2C," *Science* 1997, 276: 1404-1407.
Locksley et al., "The TNG and TNF receptor superfamilies: Integrating mammalian biology," *Cell*, 2001, 104: 487-501.
Lutz et al., "Nucleoside diphosphate kinase-mediated activation of heterotrimeric G proteins," *Meth. Enzymol.*, 2004, 390:403-418.
Maltsev et al., "Cardiomyocytes differentiated in vitro from embryonic stem cells developmentally express cardiac-specific genes and ionic currents," *Circulation Research*, 1994, 75: 233-244.
Mangi et al., "Mesenchymal stem cells modified with Akt prevent remodeling and restore performance of infarcted hearts," *Nature Medicine*, 2003, 9: 1195-1201.
Menasche et al., "Autologous skeletal myoblast transplantation for severe postinfarction left ventricular dysfunction," *J. Am. Coll. Cardiol.*, 2003, 41:1078-1083.
Menasché , "Embryonic stem cells pace the heart," *Nat. Biotechnol.*, 2004, 22(10):1237-1238.
Méry et al., "Commitment of embryonic stem cells toward a cardiac lineage: molecular mechanisms and evidence for a promising therapeutic approach for heart failure," *J. Muscle Res. Cell Motility*, 2003, 24:269-274.
Meyer et al., "A fluorescent reporter gene as a marker for ventricular specification in ES-derived cardiac calls," *FEBS Letters*, 2000, 478: 151-158.
Min et al., "Long-term improvement of cardiac function in rats after infarction by transplantation of embryonic stem cells," *J. Thoracic Cardiovasc. Surg.*, 2003, 125:361-369.
Min et al., "Transplantation of embryonic stem cells improves cardiac function in postinfarcted rats," *J. Appl. Physiol.*, 2002, 92:288-296.
Mohri et al., "Expression of cofilin isoforms during development of mouse striated muscles," *J. Muscle Res. Cell. Motil.*, 2000, 21:49-57.
Mummery et al., "Differentiation of Human Embryonic Sten Cells to Cardiomyocytes. Role of Coculture with Visceral endoderm-like cells," *Circulation*, 2003, 107:2733-2740.
Murry et al., "Cellular therapies for myocardial infarct repair," *Cold Spring Harbor Symp. Quant. Biol.*, 2002, 67:519-526.
Murry et al., "Hematopoietic stem cells do not transdifferentiate into cardiac myocytes in myocardial infarcts," *Nature*, 2004, 428:664-668.
Nakano et al., "Tumor necrosis factor-alpha confers resistance to hypoxia injury in the adult mammalian cardiac myocytes," *Circulation*, 1998, 97: 1392-1400.

(56) References Cited

OTHER PUBLICATIONS

Nir et al., "Human embryonic stem cells for cardiovascular repair," *Cardiovasc. Res.*, 2003, 58:313-323.

Nygren et al., "Bone marrow-derived hematopoietic cells generate cardiomyocytes at a low frequency through cell fusion, but not transdifferentiation," *Nat. Med.*, 2004, 10(5):494-501.

Obinata et al., "Low molecular-weight G-actin binding proteins involved in the regulation of actin assembly during myofibrillogenesis," *Cell Struct. Funct.*, 1997, 22:181-189.

O'Cochlain et al., "Transgenic overexpression of human *DMPK* accumulates into hypertrophic cardiomyopathy, myotonic myopathy and hypotension traits of myotonic dystrophy," *Human Molecular Genetics*, 2004, 13(20): 2505-2518.

Oh et al., "Cardiac progenitor cells from adult myocardium: Homing, differentiation, and fusion after infarction," *Proc. Natl. Acad. Sci. USA*, 2003, 100:12313-12318.

Olson and Schneider, "Sizing up the heart: Development redux in disease," *Genes Dev.*, 2003,17:1937-1956.

Orlic et al., "Bone marrow cells regenerate infarcted myocardium," *Nature*, 2001, 410:701-705.

Orlic et al., "Stem cells for myocardial regeneration," *Circ. Res.*, 2002, 91:1092-1102.

Perez-Terzic et al., "Directed inhibition of nuclear import in cellular hypertrophy," *J. Biological Chemistry*, 2001, 276(23): 20566-20571.

Perez-Terzic et al., "Structural Adaptation of the Nuclear Pore Complex in Stem Cell-Derived Cardiomyocytes," *Circ. Res.*, 2003, 92:444-452.

Perin et al., "Improved Exercise Capacity and Ischemia 6 and 12 Months After Transendocardial Injection of Autologous Bone Marrow Mononuclear Cells for Ischemic Cardiomyopathy," *Circulation*, 2004, 110(suppl II):II-213-II-218.

Pittenger and Martin, "Mesenchymal Stem Cells and Their Potential as Cardiac Therapeutics," *Cir. Res.*, 2004, 95:9-20.

Rajasingh et al., "STAT3-dependent mouse embryonic stem cell differentiation into cardiomyocytes analysis of molecular signaling and therapeutic efficacy of cardiomyocyte precommitted mES transplantation in a mouse model of myocardial infarction," *Circulation Research*, 2007, 101(9): 910-918.

Rangappa et al., "Cardiomyocyte-mediated contact programs human mesenchymal stem cells to express cardiogenic phenotype," *J. Thorac. Cardiovasc. Surg.*, 2003, 126:124-132.

Rudy-Reil and Lough, "Avian Precardiac Endoderm-Mesoderm Induces Cardiac Myocyte Differentiation in Murine Embryonic Stem Cells," *Circ. Res.*, 2004, 94:e107-e116.

Sachinidis et al., "Cardiac specific differentiation of mouse embryonic stem cells," *Cardiovasc Res.*,2003, 58:278-291.

Sadygov et al., "Large-scale database searching using tandem mass spectra: Looking up the answer in the back of the book," *Nature*, 2004, 1(3): 195-202.

Sauer et al., "Involvement of reactive oxygen species in cardiotrophin- 1-induced roliferation of cardiomyocytes differentiated from murine embryonic stem cells," *Exp. Cell. Res.*, 2004, 294: 313-324.

Schächinger et al., "Transplantation of Progenitor Cells and Regeneration Enhancement in Acute Myocardial Infarction. Final One-Year Results of the TOPCARE-AMI Trial," *J. Am. Coll. Cardiol.*, 2004, 44(8):1690-1699.

Seino and Mike, "Physiological and pathophysiological roles of ATP-sensitive K+ Channels," *Biophysics & Molecular Biology*, 2003, 81: 133-176.

Shachauf et al., "MYC inactivation uncovers pluripotent differentiation and tumour dormancy in hepatocellular cancer," *Nature* 2004, 431: 1112-1117.

Shevchenko et al., "Mass spectrometric sequencing of proteins from silver-stained polyacrylamide gels," *Anal. Chem*, 1996, 68: 850-858.

Shim et al., "Ex vivo differentiation of human adult bone marrow stem cells into cardiomyocyte-like cells," *Biochem. Biomes. Res. Commun.*, 2004, 324:481-488.

Sivasubramanian et al., "Left ventricular remodeling in transgenic mice with cardiac restricted overexpression of tumor necrosis factor," *Circulation*, 2001, 104: 826-831.

Smart et al., "A differential screen for putative targets of the bHLH transcription facto Handl in cardian morphogenesis," *Gene Expr. Patterns*, 2002, 2:61-67.

Solloway and Harvey, "Molecular pathways in myocardial development: a stem cell perspective," *Cardiovasc. Res.*, 2003, 58:264-277.

Srivasta et al., "A genetic blueprint for cardiac development," *Nature*, 2000, 407: 221-226.

Takeda et al., "Can the life span of human marrow stromal cells be prolonged by bmi-1, E6, E7, and/or telomerase without affecting cardiomyogenic differentiation?" *J. Gene Med.*, 2004, 6(8):833-845.

Terzic et al., "Structural adaptation of the nuclear pore complex in stem cell-derived cardiomyocytes," 2003, *Circ. Res.*, 92:444-452.

Thompson et al., "Comparison of intracardiac cell transplantation: autologous skeletal myoblasts versus bone marrow cells," *Circulation*, 2003, 108:II264-II271.

Thomson et al., "Embryonic stem cell lines derived from human blastocysts," *Science*, 1998, 282:1145-1147.

Toma et al., "Human Mesenchymal stem Cells Differentiate to a Cardiomyocyte Phenotype in the Adult Murine Heart," *Circulation*, 2002, 105:93-98.

Tomita et al., "Autologous Transplantation of Bone Marrow Cells Improves Damaged Heart Function," *Circulation*, 1999, 100(suppl. II):II-247-II-256.

Towbin and Bowles, "The failing heart," *Nature*, 2002, 415:227-233.

Tsuji, H., et al., "Amniotic Membrane-Derived Stem Cell, Supplemental materials, Figure Legends for Supplemental Material," 205260-R3, pp. 1-26 (2009).

Tsuji, H., et al., "Xenografted Human Amniotic Membrane-Derived Mesenchymal Stem Cells Are Immunologically Tolerated and Transdifferentiated Into Cardiomyocytes," Circulation Research, 106:1613-1623 (2010).

Vassilopoulos et al., "Transplanted bone marrow regenerates liver by cell fusion," *Nature*, 2003, 422: 901-904.

Wang et al., "Cell fusion is the principal source of bone-marrow-derived hepatocytes," *Nature*, 2003,422: 897-901.

Wojakowski et al., "Mobilization of CD34/CXCR4+, CD34/CD117+, c-met+ stem cells and mononuclear cells expressing early cardiac, muscle, and endothelial markers into peripheral blood in patients with acute myocardial infarction," *Circ.*, 2004, 110: 3213-3220.

Wollert and Drexler, "Mesenchymal stem cells for myocardial infarction: Promises and Pitfalls," *Circ. Res.*, 2005, 96:151-163.

Wollert and Drexler, "Clinical Applications of Stem Cells for the Heart," *Circ. Res.*, 2005, 96:151-163.

Wollert et al., "Intracoronary autologous bone-marrow cell transfer after myocardial infarction: the BOOST randomised controlled clinical trial," *Lancet*, 2004, 364:141-148.

Wu et al., "Small molecules that induce cardiomyogenesis in embryonic stem cells," *J. Am. Chem. Soc.* 2004, 126(6): 1590-1591.

Xaymardan et al., Platelet-Derived Growth Factor-AB Promotes the Generation of Adult Bone Marrow-Derived Cardiac Myocytes, *Circ. Res.*, 2004, 94:e39-e45.

Xin et al., "Oestrogen protects FKBP12.6 null mice from cardiac hypertrophy," *Nature*, 2002, 416:334-338.

Xu et al., "Mesenchymal Stem Cells from Adult Human Bone Marrow Differentiate into a Cardiomyocyte Phenotype In Vitro," *Exp. Biol. Med.*, 2004, 229:623-631.

Yang et al., "VEGF enhances functional improvement of postinfarcted hearts by transplantation of ESC-differentiated cells," *J. Appl. Physiol.*, 2002, 93: 1140-1151.

Yoon et al., "Myocardial regeneration with bone-marrow-derived stem cells," *Biol. Cell*, 2005, 97:253-263.

Zhao et al., "Human amniotic mesenchymal cells have some characteristics of cardiomyocytes," *Transplantation*, 2005, 79: 528-535.

Zingman et al., Tandem function of nucleotide binding domains confers competence to sultonylurea receptor in gating ATP-sensitive K+ channels, *J. Biol. Chem.*, 2002, 277(16): 14206-14210.

Abbott et al., "Stromal Cell—Derived Factor-1 Plays a Critical Role in Stem Cell Recruitment to the Heart After Myocardial Infarction

(56) References Cited

OTHER PUBLICATIONS but Is Not Sufficient to Induce Homing in the Absence of Injury," *Circulation*, 2004, 110:3300-3305.
Abdel-Latif et al., "Adult bone marrow-derived cells for cardiac repair: a systematic review and meta-analysis," *Arch intern Med.*, 2007, 167:989-997.
Assmus et al. "Transcoronary transplantation of progenitor cells after myocardial infarction," *N. Engl. J. Med.*, 2006, 355:1222-1232.
Ayach et al. "CXCR4 improves cardiac remodeling and neovascularization and regulated inflammatory and progenitor stem cell mobilization post-myocardial infarction," *J. Cardial Failure*,2006, 12(6):S43 (Abstract only).
Baba et al. "Flk1 + cardiac stem/progenitor cells derived from embryonic stem cells improve cardiac function in a dilated cardiomyopathy mouse model," *Cardiovasc. Res.*, 2007, 76(1):119-131.
Baldwin et al. "Myogenic cytodifferentiation of the precardiac mesoderm in the rat," *Differentiation*,1991, 47:163-172.
Barabasi and Oltvai. "Network biology: understanding the cell's functional organization," *Nat. Rev. Genet.*, 2004, 5:101-113.
Bartunek et al. "Pretreatment of bone marrow mesenchymal stem cells with cardiomyogenic adult growth factors and repair of the chronically infarcted myocardium," *Am. J. Phys: Heart and Circ. Phys.*, 2007, 292 (2):H1095-H1104.
Behfar et al. "Guided Cardiopoiesis Enhances Therapeutic Benefit of Bone Marrow Human Mesenchymal Stem Cells in Chronic Myocardial Infarction," *J. Amer. College of Cardiology*, 2010, 56(9):721-734.
Behfar et al. "Guided stem cell cardiopoietic: Discovery and translation," *J Mol and Cell Cardioogy*, 2008, 45:523-529.
Behfar et al. "Administration of Allogenic Stem Cells Dosed to Secure Cardiogenesis and Sustained Infarct Repair," *Ann. N.Y. Acad. Sci.*, 2005, 1049:189-198.
Beqqali et al. "Genome-wide transcriptional profiling of human embryonic stem cells differentiating to cardiomyocytes," *Stem Cells*, 2006, 24:1956-1967.
Brewer et al. "GATA factors lie upstream of Nkx 2.5 in the transcriptional regulatory cascade that effects cardiogenesis," *Stem Cells Dev.*, 2005, 14:425-439.
Buckingham et al. "Building the mammalian heart from two sources of myocardial cells," *Nat. Rev. Genet.*, 2005, 6:826-835.
Ceradini and Gurtner. "Homing to hypoxia: HIF-1 as a mediator of progenitor cell recruitment to injured tissue," *Trends Cardiovasc. Med.*, 2005, 15:57-63.
Ceradini et al. "Progenitor cell trafficking is regulated by hypoxic gradients through HIF-1induction of SDF-1," *Nat. Med.*, 2004, 10:858-864.
Chen et al. "Myocardin: a component of a molecular switch for smooth muscle differentiation," *J. Mol. Cell Cardiol.*, 2002, 34:1345-1356.
Chung et al. "Mitochondrial oxidative metabolism is required for the cardiac differentiation of stem cells," *Nat. Clin. Pract. Cardiovasc. Med.*, Feb. 2007, 4Suppl(1):S60-S67.
Compernolle et al. "Cardia bifida, defective heart development and abnormal neural crest migration in embryos lacking hypoxia-inducible factor-1α," *Cardiovasc. Res.*, 2003, 60:569-579.
Diaz and Gulino. "WHIM syndrome: a defect in CXCR4 signaling," *Curr. Allergy Asthma Rep.*, 2005, 5:350-355.
Eisenberg and Eisenberg. "An in vitro analysis of myocardial potential indicates that phenotypic plasticity is an innate property of early embryonic tissue," *Stem Cells Dev.*, 2004, 13:614-624.
Ema et al. "Deletion of the selection cassette, but not cis-acting elements, in targeted Flk1-lacZ allele reveals Flk1 expression in multipotent mesodermal progenitors," *Blood*, 2006, 107:111-117.
Faustino et al. "Genomic chart guiding embryonic stem cell cardiopolesis," *Genome Biol.*, 2008, 9(1):R6.
Felgner et al. "Enhanced gene delivery and mechanism studies with a novel series of cationic lipid formulations," *J. Biol. Chem.*, 1994, 269:2550-2561.
Filipczyk et al. "Cardiovascular development: towards biomedical applicability; Regulation of cardiomyocyte differentiation of embryonic stem cells by extracellular signaling," *CMLA Cellular and Molec. Life Sciences*, 2007, 64(6):704-718.
Gorlin et al. "WHIM syndrome, an autosomal dominant disorder: clinical, hematological, and molecular studies," *Am. J. Med. Genet.*, 2000, 91:368-376.
Hartmann et al. "The role of adhesion molecules and chemokine receptor CXCR4 (CD 184) in small cell lung cancer," *J. Biol. Regul. Homeost. Agents.*, 2004, 18:126-130.
Hernandez et al. "Mutations in the chemokine receptor gene CXCR4 are associated with WHIM syndrome, a combined immunodeficiency disease," *Nat. Genet.*, 2003, 34:70-74.
Huber et al. "Haemangioblast commitment is initiated in the primitive streak of the mouse embryo," *Nature*, 2004, 432:625-630.
Janssens et al. "Autologous bone marrow-derived stem-cell transfer in patients with ST-segment elevation myocardial infarction: double-blind, randomised controlled trial," *Lancet*, 2006, 367:113-121.
Kattman et al. "Multipotent flk-1(+) cardiovascular progenitor cells give rise to the cardiomyocyte, endothelial, and vascular smooth muscle lineages," *Dev. Cell*, 2006, 11:723-732.
Kawai et al. "Efficient cardiomyogenic differentiation of embryonic stem cell by fibroblast growth factor 2 and bone morphogenetic protein 2," *Circ. J.*, 2004, 68:691702.
Kay et al. "Gene therapy," *Proc. Natl. Acad. Sci. USA*, 1997, 94:12744-12746.
Kirby. "Molecular embryogenesis of the heart," *Pediatr. Dev. Pathol.*, 2002, 5:516-543.
Kofidis et al. "Insulin-like growth factor promotes engraftment, differentiation, and functional improvement after transfer of embryonic stem cells for myocardial restoration," *Stem Cells*, 2004, 22:1239-1245.
Kolossov et al. "Engraftment of engineered ES cell-derived cardiomyocytes but not BM cells restores contractile function to the infarcted myocardium," *J. Exp. Med.*, 2006, 203:2315-2327.
Kucia et al. "Bone marrow as a source of circulating CXCR4+ tissue-committed stem cells," *Biol. Cell*, 2005, 97:133-146
Kucia et al. "Trafficking of normal stem cells and metastasis of cancer stem cells involve similar mechanisms: pivotal role of the SDF-I-CXCR4 axis," *Stem Cells*, 2005, 23:879-894.
Kulbe et al. "The chemokine network in cancer—much more than directing cell movement," *Int. J. Dev. Biol.*, 2004, 48:489-496.
Laflamme and Murry. "Regenerating the heart," *Nat. Biotechnol.*, 2005, 23:845-856.
Lapidot and Kollet. "The essential roles of the chemokine SDF-1 and its receptor CXCR4 in human stem cell homing and repopulation of transplanted immune-deficient NOD/SCID and NOD/SCID/B2m(null) mice," *Leukemia*, 2002, 16:1992-2003.
Lapidot et al. "How do stem cells find their way home?" *Blood*, 2005, 106:1901-1910.
Lapidot, "Mechanism of human stem cell migration and repopulation of NOD/SCID and B2mnull NOD/SCID mice. The role of SDF-1/CXCR4 interactions," *Ann. N.Y. Acad. Sci.*, 2001, 938:83-95.
Lough and Sugi. "Endoderm and heart development," *Dev. Dyn.*, 2000, 217:327-342.
Lough et al. "Combined BMP-2 and FGF-4, but neither factor alone, induces cardiogenesis in non-precardiac embryonic mesoderm," *Dev. Biol.*, 1996, 178:198-202.
Lunde et al. "Intracoronary injection of mononuclear bone marrow cells in acute myocardial infarction," *N. Engl. J. Med.*, 2006, 355:1199-1209.
McGrath et al. "Embryonic expression and function of the chemokine SDF-1 and its receptor, CXCR4," *Dev. Biol.*, 1999, 213:442-456.
Menard et al. "Transplantation of cardiac-committed mouse embryonic stem cells to infarcted sheep myocardium: a preclinical study," *Lancet*, 2005, 366:1005-1012.
Meyer et al. "Intracoronary bone marrow cell transfer after myocardial infarction: eighteen months' follow-up data from the randomized, controlled BOOST (BOne marrOw transfer to enhance ST-elevation infarct regeneration) trial," *Circulation*, 2006, 113:1287-1294.

(56) References Cited

OTHER PUBLICATIONS

Molkentin et al. "Direct activation of a GATA6 cardiac enhancer by Nkx2.5: evidence for a reinforcing regulatory network of Nkx2.5 and GATA transcription factors in the developing heart," *Dev. Biol.*, 2000, 217:301-309.

Moretti et al. "Multipotent embryonic isl1 + progenitor cells lead to cardiac, smooth muscle, and endothelial cell diversification," *Cell*, 2006, 127:1151-1165.

Mummery et al. "Cardiomyocyte differentiation of mouse and human embryonic stem cells," *J. Anatomy*, 2002, 200(part 3):233-242.

Nagasawa et al. "Defects of B-celllymphopoiesis and bone-marrow myelopoiesis in mice lacking the CXC chemokine PBSF/SDF-1," *Nature*, 1996, 382:635-638.

Nakajima et al. "Transplantation of Flk1-postitive embryonic stem cells improves cardiac function after acute myocardial infarction in mice," *J. Heart and Lung Transplant.*, 2005, 24(2):S94 (Abstract only).

Nelson et al. "Improved cardiac function in infarcted mice after treatment with pluripotent embryonic stem cells," *Anat. Rec.*, 2006, 288:1216-1224.

Nelson et al. "CXCR4 (+)/FLK-1 (+) biomarkers select a cardiopoietic lineage from embryonic stem cells," *Stem Cells*, 2008, 26(6):1464-1473.

Nichols et al. "Formation of pluripotent stem cells in the mammalian embryo depends on the POU transcription factor OCt4," *Cell*, 1998, 95: 379-391.

Perez-Terzic et al. "Stem cells transform into a cardiac phenotype with remodeling of the nuclear transport machinery," *Nat. Clin. Pract. Cardiovasc. Med.*, 2007, 4(Suppl 1):S68-S76.

Pillarisetti and Gupta. "Cloning and relative expression analysis of rat stromal cell derived factor-1 (SDF-1)1: SDF-1 alpha mRNA is selectively induced in rat model of myocardial infarction," *Inflammation*, 2001, 25:293-300.

Rosenzweig. "Cardiac cell therapy—mixed results from mixed cells," *N. Engl. J Med.*, 2006,355:1274-1277.

Sanchez et al. "Contemplating the bright future of stem cell therapy for cardiovascular disease," *Nat. Clin. Pract. Cardiovasc. Med.*, 2006, 3 Suppl.(1):S138-S151.

Schachinger et al. "Intracoronary bone marrow-derived progenitor cells in acute myocardial infarction," *N. Engl. J. Med.*, 2006, 355:1210-1221.

Singla et al. "Transplantation of embryonic stem cells into the infarcted mouse heart: formation of multiple cell types," *J. Mol. Cell. Cardiol.*, 2006, 40:195-200.

Smith et al "Inhibition of pluripotential embryonic stem cell differentiation by purified polypeptides," *Nature*, 1988, 336:688-690.

Srivastava and Ivey. "Potential of stem-cell-based therapies for heart disease," *Nature*, 2006, 441:1097-1099.

Srivastava. "Making or breaking the heart: from lineage determination to morphogenesis," *Cell*, 2006, 126:1037-1048.

Sugi and Lough. "Activin-A and FGF-2 mimic the inductive effects of anterior endoderm on terminal cardiac myogenesis in vitro," *Dev. Biol.*, 1995, 168:567-574.

Tada et al. "Characterization of mesendoderm: a diverging point of the definitive endoderm and mesoderm in embryonic stem cell differentiation culture," *Development*, 2005, 132:4363-4374.

Taniuchi et al. "Dizygotic twin sisters with myelokathexis: mechanism of its neutropenia," *Am. J. Hematol.*, 1999, 62:106-111.

Torella et al. "Cardiac stem cells regenerate the infarcted heart, restoring function and long-term survival in mice," *Circulation*, 2004, 110(17), Suppl III, 4 pages, (Abstract only; abstract on last page).

Vandervelde et al. "Signaling factors in stem cell-mediated repair of infarcted myocardium," *J. Mol. Cell Cardiol.*, 2005, 39:363-376.

Wobus et al. "Retinoic acid accelerates embryonic stem cell-derived cardiac differentiation and enhances development of ventricular cardiomyocytes," *J. Mol. Cell Cardiol.*, 1997, 29:1525-1539.

Wu et al. "Developmental origin of a bipotential myocardial and smooth muscle cell precursor in the mammalian heart," *Cell*, 2006, 127:1137-1150.

Yamaguchi et al. "flk-1, an flt-related receptor tyrosine kinase is an early marker for endothelial cell precursors," *Development*, 1993, 118:489-498.

Yamashita et al. "Differentiation and diversification of vascular cells from embryonic stem cells," *Int. J. Hematol.*, 2004, 80(6808):92-96.

Yamashita et al. "Flk1 -positive cells derived from embryonic stem cells servie as vascular progenitors," *Nature*, Nov. 2, 2000, 408:92-96.

Yamashita et al. "Perspective identification of cardiac progenitors by a novel single cell-based cardiomyocyte induction," *FASEB Journal*, 2005, 19:1534-1536.

Yasunaga et al. "Induction and monitoring of definitive and visceral endoderm differentiation of mouse ES cells," *Nat. Biotechnol.*, 2005, 23:1542-1550.

Yuasa et al. "Transient inhibition of BMP signaling by Noggin induces cardiomyocyte differentiation of mouse embryonic stem cells," *Nat. Biotechnol.*, 2005, 23:607-611.

Yusuf et al. "Expression of chemokine receptor CXCR4 during chick embryo development," *Anat. Embryol. (Berl)*, 2005, 210:35-41.

Zaffran and Frasch. "Early signals in cardiac development," *Circ. Res.*, Sep. 20, 2002, 91(6):457-469.

Zaffran et al. "Cardioblast-intrinsic Tinman activity controls proper diversification and differentiation of myocardial cells in *Drosophila*," *Development*, 2006, 133:4073-4083.

Zhu et al. "Evidence that FGF receptor signaling is necessary for endoderm-regulated development of precardiac mesoderm," *Mech. Ageing Dev.*, 1999, 108:77-85.

Zou et al. "Function of the chemokine receptor CXCR4 in haematopoiesis and in cerebellar development," *Nature*, 1998, 393:595-599.

Zingman et al. "Kir6.2 is required for adaptation to stress," *PNAS*, 2002, 99(20): 13278-13283.

Extended European Search Report in European Application No. 09763198.0, dated Jun. 13, 2012, 11 pages.

Extended European Search Report in European Application No. 10179541.7, dated Nov. 24, 2010, 9 pages.

Extended European Search Report in European Application No. 08731697.2, dated Mar. 10, 2011, 8 pages.

International Search Report and Written Opinion in International Application No. PCT/US2009/044714, dated Feb. 25, 2010, 16 pages.

International Preliminary Report on Patentability in International Application No. PCT/US2009/044714, mailed Dec. 9, 2010, 9 pages.

International Search Report and Written Opinion in International Application No. PCT/US2009/044751, dated Feb. 17, 2010, 14 pages.

International Search Report and Written Opinion in International Application No. PCT/US2010/035616, dated Aug. 3, 2010, 13 pages.

International Preliminary Report on Patentability in International Application No. PCT/US2010/035616, dated Jul. 5, 2011, 10 pages.

International Preliminary Report on Patentability in PCT/US2008/056248, issued Sep. 8, 2009, 6 pages.

International Search Report and Written Opinion of the International Searching Authority in PCT/US2008/056248, mailed Jun. 23, 2008, 11 pages.

International Preliminary Report on Patentability in International Application No. PCT/US2008/064895, mailed Dec. 9, 2010, 7 pages.

International Search Report and Written Opinion in International Application No. PCT/US2008/064895, mailed Feb. 24, 2009, 13 pages.

International Preliminary Report on Patentability in International Application No. PCT/US2005/026800, mailed Apr. 26, 2007, 6 pages.

International Search Report and Written Opinion in International Application No. PCT/US2005/026800, Mar. 28, 2007, 12 pages.

"AMOS 5 Correlation" http://www.math.ntua.gr/fouskakis/SS/correlation.pdf (Jul. 7, 2013).

Levsky et al. (2002) Science, vol. 297, pp. 836-840.

* cited by examiner

COMPOSITIONS AND METHODS FOR OBTAINING CELLS TO TREAT HEART TISSUE

CROSS-REFERENCE TO RELATED APPLICATIONS

This application is a National Stage application under 35 U.S.C. 371 and claims benefit under 35 U.S.C. 119(a) of International Application No. PCT/US2009/044714, having an International Filing Date of May 20, 2009, which claims the benefit of priority from International Application Serial No. PCT/US2008/064895, filed on May 27, 2008.

TECHNICAL FIELD

This document relates to methods and materials involved in obtaining and using cardiac cells. For example, this document relates to methods and materials for providing mammalian heart tissue with cells (e.g., differentiated cardioprogenitor cells or cardiopoietic cells) that incorporate into the heart tissue as functional cardiomyocytes.

BACKGROUND INFORMATION

Cardiovascular disease is a leading cause of morbidity and mortality worldwide, despite advances in patient management. In contrast to tissues with high reparative capacity, heart tissue is vulnerable to irreparable damage. Cell-based regenerative cardiovascular medicine is, therefore, being pursued in the clinical setting.

The recent advent of stem cell biology extends the scope of current models of practice from traditional palliation towards curative repair. Typically, clinical experience has been based on adult stem cells recruited from autologous sources and delivered in an unaltered state. First generation biologics are naïve human stem cells, identified as readily accessible cytotypes. It has been shown that particular individuals improve on delivery of naïve human stem cells.

DEFINITIONS

Within the frame of the present document, and unless indicated to the contrary, the terms designated below between quotes have the following definitions.

The term 'hMSCs' means human mesenchymal stem cells.

The 'cardio-generative potential' of a cell designates the ability of this cell to succeed to generate cardiac cells for instance myocardium, when injected into an infracted heart.

'Cardiopoietic cells' (CP) are cells engaged in the way of differentiation from a non-differentiated cell. A 'cardiopoietic cell' exhibits a cardiac differentiation defined by nuclear translocation of the early cardiac transcription factor Nkx2.5 and the late cardiac transcription factor MEF2C (Behfar et al. Derivation of a cardiopoietic population from human mesenchymal stem yields progeny, Nature Clinical Practice, Cardiovascular Medicine, March 2006 vol. 3 supplement 1, pages S78-S82). Nuclear translocation of cardiac transcription factor GATA4 can be observed. Cardiopoietic cells can lack sarcomeres and can lack expression of sarcomeric proteins. A cardiopoietic cell keeps the capacity to divide itself. Cardiopoietic cells are also called 'cardiomyocyte precursors' or 'cardiomyocyte progenitor cells' because they may differentiate into cardiomyocytes. In the context of the present document, cardiopoietic cells may be derived from human adult mesenchymal stem cells (hMSCs). 'CP-hMSCs' designates such cardiopoietic cells derived from human adult mesenchymal stem cells.

A 'cocktail' or 'cardiogenic cocktail' designates a composition containing at least two cardiogenic substances.

A 'cardiogenic substance' is a substance which improves the cardio-generative potential of a cell.

A 'cocktail-guided cell' or 'cell guided towards cardiopoiesis' is a cell which has been put into contact with a cocktail and further enters into differentiation.

The 'differentiation' is the process by which a less specialized cell becomes a more specialized cell.

The 'ejection fraction' means the fraction of blood pumped out during a heart beat. Without a qualifier, the term ejection fraction refers specifically to that of the left ventricle (left ventricular ejection fraction or LVEF).

The 'change of ejection fraction' means the difference between ejection fraction of the heart of an animal treated with cells injected into its infarcted heart, measured after a given time and the ejection fraction measured prior to injection.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

SUMMARY

The invention relates to compositions comprising TGFβ-1, BMP4, α-thrombin, a compound selected from the group consisting of Cardiotrophin and IL-6, and a compound selected from the group consisting of Cardiogenol C and retinoic acid. In a preferred embodiment, the compositions of the invention comprise TGFβ-1, BMP4, α-thrombin, Cardiotrophin and Cardiogenol C. The compositions of the invention may comprise at least one compound selected from the group consisting of FGF-2, IGF-1, Activin-A, TNF-α, FGF-4, LIF, VEGF-A and combinations thereof. They may also comprise FGF-2, IGF-1 and Activin-A. Other preferred compositions of the invention comprises Activin-A, FGF-2, IL-6, IGF-1 and retinoic acid. According to an alternative embodiment, the compositions of the invention can lack at least one compound chosen in the group consisting of TNF-α, FGF-4, LIF, and VEGF-A.

When one of the following compounds is present in a composition of the invention, it may be present in an amount of between 1 and 5 ng of said TGFβ-1 per ml, between 1 and 10 ng of said BMP4 per ml, between 0.5 and 5 ng of said Cardiotrophin per ml, between 0.5 and 5 units of said α-thrombin per ml, and between 50 and 500 nM of said Cardiogenol C, between 1 and 10 ng of said FGF-2 per ml, between 10 and 100 ng of said IGF-1 per ml, between 1 and 50 ng of said Activin-A per ml, between 1 and 50 ng of said TNF-α per ml, between 1 and 20 ng of said FGF-4 per ml, between 10 and 100 ng of said IL-6 per ml, between 1 and 10 units of said LIF per ml, between 1 and 50 ng of said VEGF-A per ml, between 0.1 and 1.0 µM of said retinoic acid per ml.

Preferred compositions according to the invention comprise recombinant TGFβ-1 (2.5 ng/ml), BMP4 (5 ng/ml), Cardiotrophin (1 ng/ml), Cardiogenol C (100 µM nM), used in a combinatorial fashion. Particularly preferred compositions of the invention comprises such compounds and further comprise α-thrombin, (1 U/ml), FGF-2 (10 ng/ml), IGF-1 (50 ng/ml) and Activin-A (5 ng/ml).

Other preferred compositions of the invention comprise recombinant TGFβ-1 (2.5 ng/ml), BMP4 (5 ng/ml), Activin-A (5 ng/ml), FGF-2 (10 ng/ml), IL-6 (100 ng/ml), Factor-IIa (hα-thrombin, 1 U/ml), IGF-1 (50 ng/ml), and retinoic acid (1 µM) used in a combinatorial fashion.

Preferably, the compositions of the invention are comprised in a medium selected from the group consisting of media containing of foetal calf serum, human serum, platelet lysate, and mixtures thereof.

The invention also relates to a method for obtaining from initial cells differentiated cells expressing an elevated level of at least one of the mRNAs selected from the group consisting of MEF2c mRNA, MESP-1 mRNA, Tbx-5 mRNA, GATA4 mRNA, Flk-1 mRNA, GATA6 mRNA, Fog-1 mRNA, and combinations thereof, and/or have at least one polypeptide selected from the group consisting of Nkx2.5 polypeptides, MEF2C polypeptides, Tbx-5 polypeptides, FOG-2 polypeptides, GATA-4 polypeptides MESP-1 polypeptides, and combinations thereof, wherein said at least one polypeptide is associated with the nuclei of said differentiated cells, wherein said method comprises culturing initial cells in the presence of a composition according to the invention In such methods, the differentiated cells express preferably an elevated level of MEF2c mRNA and MESP-1 mRNA.

In a preferred embodiment of the invention, the initial cells are mesenchymal stem cells. Such cells can be bone marrow-derived stem cells. They can express CD90, CD105, CD133, CD166, CD29, and CD44 on the cell surface and do not express CD14, CD34, and CD45 on the cell surface.

Most preferably, the differentiated cells are cardiopoietic cells.

Another aspect of the invention is a method for delivering differentiated cells to a mammal, wherein said method comprises:
(a) determining that a sample of cells from a population of differentiated cells comprises cells that express an elevated level of at least one of the mRNA selected from the group consisting of MEF2c mRNA, MESP-1 mRNA, Tbx-5 mRNA, GATA4 mRNA, Flk-1 mRNA, GATA6 mRNA, Fog-1 mRNA, and combinations thereof, and/or have at least one polypeptide selected from the group consisting of Nkx2.5 polypeptides, MEF2C polypeptides, Tbx-5 polypeptides, MESP-1 polypeptides, GATA-4 polypeptides, FOG-2 polypeptides, and combinations thereof, wherein said polypeptide is associated with the nuclei of said differentiated cells, and
(b) administering cells from said population of differentiated cells to said mammal. Said population of differentiated cells can be obtained from said original cells cultured in the presence of any of said compositions according to the invention. In a particular embodiment, said step (a) may comprise using a reverse transcription polymerase chain reaction or using immunocytochemistry. Said administering step comprises may comprise administering said cells via an administration selected from the group consisting of systemic, intracardiac, and intracoronary administrations.

Another aspect of the invention is a method for providing heart tissue with cardiomyocytes, wherein said method comprises administering, to said heart tissue, said differentiated cells of claims obtainable by contact with a composition according to the invention.

Details of one or more embodiments of the invention are set forth in the accompanying drawings and the description below. Other features, objects, and advantages of the invention will be apparent from the description and from the claims.

DETAILED DESCRIPTION

This document provides methods and materials related to cardiac cells (e.g., differentiated cardioprogenitor cells). For example, this document provides cells having the ability to incorporate into heart tissue as functional cardiomyocytes, methods for making such cells, compositions for making such cells, and methods for determining whether or not a population of cells (e.g., differentiated cardioprogenitor cells) contains cells having the ability to incorporate into heart tissue as functional cardiomyocytes. This document also provides methods and materials for providing heart tissue (e.g., human heart tissue) with functional cardiomyocytes.

The differentiated cardioprogenitor cells provided herein can be from any species including, without limitation, humans, monkeys, horses, dogs, cats, rats, or mice. For example, differentiated cardioprogenitor cells can be mammalian (e.g., human) differentiated cardioprogenitor cells.

In some cases, differentiated cardioprogenitor cells provided herein have the ability to incorporate into heart tissue as functional cardiomyocytes.

Any appropriate method can be used to obtain differentiated cardioprogenitor cells. For example, differentiated cardioprogenitor cells can be derived from stem cells such as mammalian (e.g., human) stem cells.

In some cases, differentiated cardioprogenitor cells can be derived from embryonic stem cells. In some cases, differentiated cardioprogenitor cells can be derived from mesenchymal stem cells. Mesenchymal stem cells can be obtained from any source. For example, mesenchymal stem cells can be obtained from mammalian (e.g., human) tissue such as bone marrow and trabecular bone. Mesenchymal stem cells can be cultured in vitro. For example, mesenchymal stem cells can be expanded in number in vitro. Mesenchymal stem cells can express or not express a polypeptide marker on the cell surface. For example, mesenchymal stem cells can express CD133, CD90, CD105, CD166, CD29, and CD44 on the cell surface and not express CD14, CD34, and CD45 on the cell surface.

Any appropriate method can be used to derive differentiated cardioprogenitor cells from stem cells (e.g., mesenchymal stem cells). For example, differentiated cardioprogenitor cells can be derived from mesenchymal stem cells by incubating the mesenchymal stem cells with a composition (e.g., culture media). The composition can be any appropriate composition containing one or more factors. The factors can be any type of factors such as polypeptides, steroids, hormones, and small molecules. Examples of such factors include, without limitation, TGFβ, BMP, FGF-2, IGF-1, Activin-A, Cardiotrophin, α-thrombin, and Cardiogenol C.

In one embodiment, media containing TGFβ, BMP, Cardiotrophin, α-thrombin, and Cardiogenol C can be used to obtain differentiated cardioprogenitor cells from stem cells (e.g., mesenchymal stem cells). In such cases, FGF-2, IGF-1, Activin-A, or a combination thereof can be added to the medium after an initial culture period (e.g., one or two days) with medium containing TGFβ, BMP, Cardiotrophin, α-thrombin, and Cardiogenol C.

TGFβ can be any polypeptide having TGFβ activity, such as human TGFβ. For example, TGFβ can be recombinant TGFβ or synthetic TGFβ. In one embodiment, TGFβ can be TGFβ-1. Any appropriate concentration of TGFβ can be used. For example, between 1 and 10 ng of TGF-β per ml (e.g., about 2.5 ng of TGFβ per ml) can be used.

BMP can be any polypeptide having BMP activity, such as human BMP. For example, BMP can be recombinant BMP or synthetic BMP. In one embodiment, BMP can be BMP4. Any concentration of BMP can be used. For example, between 1 and 20 ng of BMP per ml (e.g., about 5 ng of BMP4 per ml) can be used.

FGF-2 can be any polypeptide having FGF-2 activity, such as human FGF-2. For example, FGF-2 can be recombinant FGF-2 or synthetic FGF-2. Any concentration of FGF-2 can be used. For example, between 1 and 20 ng of FGF-2 per ml (e.g., about 5 ng of FGF-2 per ml) can be used.

IGF-1 can be any polypeptide having IGF-1 activity, such as human IGF-1. For example, IGF-1 can be recombinant IGF-1 or synthetic IGF-1. Any concentration of IGF-1 can be used. For example, between 10 and 100 ng of IGF-1 per ml (e.g., about 50 ng of IGF-1 per ml) can be used.

Activin-A can be any polypeptide having Activin-A activity, such as human Activin-A. For example, Activin-A can be recombinant Activin-A or synthetic Activin-A. Any concentration of Activin-A can be used. For example, between 1 and 50 ng of Activin-A per ml (e.g., about 10 ng of Activin-A per ml) can be used.

α-Thrombin can be any polypeptide having α-thrombin activity, such as human α-thrombin. For example, α-thrombin can be recombinant α-thrombin or synthetic α-thrombin. Any concentration of α-thrombin can be used. For example, between 0.5 and 10 units of α-thrombin per ml (e.g., about 1 unit of α-thrombin per ml) can be used.

Cardiotrophin can be any polypeptide having Cardiotrophin activity, such as human Cardiotrophin-1. For example, Cardiotrophin can be recombinant Cardiotrophin or synthetic Cardiotrophin. Any concentration of Cardiotrophin can be used. For example, between 0.5 and 10 ng of Cardiotrophin per ml (e.g., about 1 ng of Cardiotrophin-1 per ml) can be used.

IL-6 can be any polypeptide having IL-6 activity, such as human IL-6. For example, IL-6 can be recombinant IL-6 or synthetic IL-6. Any concentration of IL-6 can be used. For example, between 100 and 200 ng of IL-6 per ml can be used.

Any concentration of Cardiogenol C or a pharmaceutically acceptable salt thereof (e.g., Cardiogenol C hydrochloride) can be used. For example, between 10 and 1000 nM of Cardiogenol C (e.g., about 100 nM of Cardiogenol C) can be used.

Retinoic acid can be any molecule having retinoic acid activity, such as synthetic retinoic acid, natural retinoic acid, a vitamin A metabolite, a natural derivative of vitamin A, or a synthetic derivative of vitamin A. Any concentration of retinoic acid can be used. For example, between $1 \times 10^{-6}$ and $2 \times 10^{-6}$ μM of retinoic acid can be used.

In some cases, serum-containing or serum-free media supplemented with TGFβ-1 (e.g., 2.5 ng/ml), BMP4 (e.g., 5 ng/ml), FGF-2 (e.g., 5 ng/ml), IGF-1 (e.g., 50 ng/ml), Activin-A (e.g., 10 ng/ml), Cardiotrophin (e.g., 1 ng/ml), α-thrombin (e.g., 1 Unit/ml), and Cardiogenol C (e.g., 100 nM) can be used to obtain differentiated cardioprogenitor cells from stem cells (e.g., mesenchymal stem cells). In some cases, the media (e.g., serum-containing or serum-free media) can contain platelet lysate (e.g., a human platelet lysate)

In some cases, the composition used to obtain differentiated cardioprogenitor cells from mesenchymal stem cells can contain additional optional factors such as TNF-α, LIF, and VEGF-A.

TNF-α can be any polypeptide having TNF-α activity, such as human TNF-α. For example, TNF-α can be recombinant TNF-α or synthetic TNF-α. Any concentration of TNF-α can be used. For example, between 5 and 50 ng of TNF-α per ml can be used.

LIF can be any polypeptide having LIF activity, such as human LIF. For example, LIF can be recombinant LIF or synthetic LIF. Any concentration of LIF can be used. For example, between 2.5 and 100 ng of LIF per ml can be used.

VEGF-A can be any polypeptide having VEGF-A activity, such as human VEGF-A. For example, VEGF-A can be recombinant VEGF-A or synthetic VEGF-A. Any concentration of VEGF-A can be used. For example, between 5 and 200 ng of VEGF-A per ml can be used.

A composition provided herein can contain any combination of factors. For example, a composition provided herein can contain TGFβ-1, BMP4, Activin-A, Cardiotrophin, α-thrombin, and Cardiogenol C. In some cases, a composition provided herein can contain TGFβ-1, BMP4, FGF-2, IGF-1, Cardiotrophin, α-thrombin, and Cardiogenol C. In some cases, a composition provided herein can contain TGFβ-1, BMP4, FGF-2, IGF-1, Cardiotrophin, α-thrombin, and Cardiogenol C. In some cases, a composition provided herein can lack TNF-α, IL-6, LIF, VEGF-A, retinoic acid, or any combination thereof (e.g., IL-6, LIF, VEGF-A, and retinoic acid; LIF, VEGF-A, and retinoic acid; or TNF-α, IL-6, LIF, and VEGF-A).

A composition provided herein can be prepared using any appropriate method. For example, a composition provided herein can be prepared using commercially available factors. In some cases, a composition provided herein can be prepared to contain cells lysates (e.g., a platelet lysate) or conditioned media from cells such as cardiomyocyte cells or TNF-α-stimulated endodermal cells. For example, a composition provided herein can be prepared using a platelet lysate supplemented with commercially available factors. In some cases, a composition provided herein can be prepared using factors isolated from conditioned medium. In some cases, the factors can be dissolved in media such as cell culture media that does or does not contain serum.

Any appropriate method can be used to incubate stem cells (e.g., mesenchymal stem cells) with a composition provided herein to obtain differentiated cardioprogenitor cells having the ability to incorporate into heart tissue as functional cardiomyocytes. For example, mesenchymal stem cells can be incubated with a composition provided herein for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days. In some cases, a composition provided herein and used to incubate mesenchymal stem cells can be replaced every day or every 2, 3, 4, 5, 6, 7, 8, 9, 10, 11, 12, 13, 14, 15, 16, 17, 18, 19, 20, 21, 22, 23, 24, 25, 30, 35, 40, 45, or 50 days.

In some cases, mesenchymal stem cells can be incubated with a composition provided herein in the presence or absence of serum. Any appropriate cell density can be used when incubating stem cells with a composition provided herein. For example, between about 1000 and 2000 mesenchymal stem cells per cm$^2$ (e.g., between about 1500-2000 cells/cm$^2$) can be incubated with a composition provided herein to obtain differentiated cardioprogenitor cells.

Once stem cells (e.g., mesenchymal stem cells) have been incubated with a composition provided herein or otherwise treated with differentiation factors, the state of differentiation can be monitored to determine whether or not the stem cells differentiated into differentiated cardioprogenitor cells having the ability to incorporate into heart tissue as functional cardiomyocytes. For example, a sample of cells can be collected and assessed using techniques such as Western blotting, fluorescence-activated cell sorting (FACS), immunostaining, laser confocal microscopy, and reverse transcription polymerase chain reaction (RT-PCR) techniques (e.g., quantitative RT-PCR). In some cases, cells found to express an elevated level of MEF2c, MESP-1, Tbx-5, Nkx2.5, GATA6, Flk-1, Fog 1 and Fog 2 polypeptides or mRNA can be selected for administration into a mammal to treat heart tissue.

As described herein, differentiated cardioprogenitor cells derived from mesenchymal stem cells cultured with a platelet lysate containing TGFß-1, BMP4, FGF-2, IGF-1, Activin-A, Cardiotrophin, α-thrombin, and Cardiogenol C exhibited a 2 to 5-fold increase in MEF2c mRNA, MESP-1 mRNA, Tbx-5 mRNA, GATA6 mRNA, Flk-1 or Fog 1 mRNA levels as compared to the levels observed with pre-treated mesenchymal stem cells. These differentiated cardioprogenitor cells also exhibited the ability to incorporate into heart tissue as functional cardiomyocytes when injected intramyocardially, subcutaneously, or intravascularly with heart pump function improvement directly correlated with structural repair in both ischemic and non-ischemic settings. Functional benefit was documented both echocardiographically in vivo, and histologically on autopsy through staining of human specific proteins. Also as described herein, differentiated cardioprogenitor cells derived from mesenchymal stem cells cultured with serum containing TGFβ-1, BMP4, FGF-2, IGF-1, Activin-A, Cardiotrophin, α-thrombin, and Cardiogenol C exhibited a 5 to 10-fold increase in MEF2c mRNA, MESP-1 mRNA, and Tbx-5 mRNA levels as compared to the levels observed with pre-treated mesenchymal stem cells.

These differentiated cardioprogenitor cells also exhibited the ability to incorporate into heart tissue as functional cardiomyocytes when injected intramyocardially (e.g., through endocardial or epicardial routes), into the coronary arteries, infused in the heart, or administered systemically (e.g., subcutaneously), with heart pump function improvement directly correlated with structural repair in both ischemic and non-ischemic settings. Functional benefit was documented by cardiac ultrasound in vivo, and by microscopic analysis on autopsy through staining of human specific proteins. Thus, release criteria such as elevated polypeptide or mRNA levels of MEF2c, MESP-1, Tbx-5, GATA6, Flk-1, Fog 1, FOG 2, or combinations thereof can be used to evaluate cells prior to administration into a mammal.

The term "elevated level" as used herein with respect to polypeptide or mRNA levels of MEF2c, MESP-1, Tbx-5, GATA6, Flk-1, or Fog (for instance FOG 1 for mRNA, FOG 2 for the polypeptide) within a cell population refers to any level that is greater than a reference level for that polypeptide or mRNA.

The term "reference level" as used herein with respect to polypeptide or mRNA levels of MEF2c, MESP-1, Tbx-5, GATA6, Flk-1, or Fog (for instance FOG 1 for mRNA, FOG 2 for the polypeptide) within a cell population refers to the level typically found in pre-treated cells (e.g., pre-treated mesenchymal stem cells). For example, an MEF2c mRNA reference level, an MESP-1 mRNA reference level, a Tbx-5 mRNA reference level, a GATA6 mRNA reference level, and a FOG 1 mRNA reference level can be the average level of MEF2c, MESP-1, Tbx-5, GATA6, Flk-1 and FOG 1 mRNA, respectively, that is present in a random sampling of mesenchymal stem cells not treated with a composition provided herein or otherwise treated with differentiation factors. It will be appreciated that levels from comparable samples are used when determining whether or not a particular level is an elevated level.

Elevated polypeptide and/or mRNA levels of MEF2c, MESP-1, Tbx-5, GATA 4, GATA6, Flk-1, Fog 2 or FOG 1 can be any level provided that the level is greater than a corresponding reference level.

For example, an elevated level of Tbx-5 mRNA can be 1.5, 2, 3, 4, 5, 6, 7, 8, 9, 10, or more fold greater than the reference level Tbx-5 mRNA observed in untreated mesenchymal stem cells. It is noted that a reference level can be any amount. For example, a reference level for Tbx-5 mRNA can be zero. In this case, any level of Tbx-5 mRNA greater than zero would be an elevated level.

In some cases, identification criteria can include microscopic analysis of cells prior to administration into a mammal. Such microscopic analysis can include assessing the cells for transcription factor polypeptides associated with the nucleus. For example, cells appropriate for release into a mammal can be assessed for the presence of Nkx2.5, MEF2c, GATA4, MESP-1, FOG 2, Tbx-5, or any combination thereof associated with the nucleus before being released into the mammal.

Any appropriate method can be used to provide heart tissue with differentiated cardioprogenitor cells having the ability to incorporate into heart tissue as functional cardiomyocytes. For example, differentiated cardioprogenitor cells can be injected intramyocardially (e.g., through endocardial or epicardial routes), into the coronary arteries, infused in the heart, or administered systemically (e.g., subcutaneously).

Any heart tissue can be provided with differentiated cardioprogenitor cells. For example, mammalian (e.g., human) heart tissue can be provided with differentiated cardioprogenitor cells. In some cases, heart tissue that has suffered from ischemic cardiomyopathy, myocardial infarction, or heart failure can be provided with differentiated cardioprogenitor cells.

Any type of differentiated cardioprogenitor cells can be administered to heart tissue. For example, autologous or heterologous differentiated cardioprogenitor cells can be administered to heart tissue. In some cases, stem cells (e.g., mesenchymal stem cells) that were incubated with a composition provided herein can be administered to heart tissue.

The stem cells can be incubated with a composition provided herein for any length of time before being administered to heart tissue. For example, the stem cells can be incubated with a composition provided herein for 6 to 24 hours (e.g., 8, 10, 12, 18, or 22 hours) or for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days before being administered to heart tissue. In some cases, stem cells that were incubated with a composition provided herein can be administered to heart tissue together with a composition provided herein.

The stem cells can be incubated with a composition provided herein for any length of time before being administered to heart tissue together with a composition provided herein. For example, the stem cells can be incubated with a composition provided herein for 6 to 24 hours (e.g., 8, 10, 12, 18, or 22 hours) or for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days before being administered to heart tissue together with a composition provided herein.

In some cases, differentiated cardioprogenitor cells can be assessed to determine whether or not they meet particular release criteria prior to being administered to a mammal. For example, differentiated cardioprogenitor cells can be assessed using RT-PCR to confirm that the differentiated cardioprogenitor cells express an elevated polypeptide or mRNA level of MEF2c, MESP-1, Tbx-5, GATA6, Flk-1, Fog, (FOG 1 for mRNA, FOG 2 for the polypeptide) or combinations thereof before being administered into a mammal.

The invention will be further described in the following examples, which do not limit the scope of the invention described in the claims.

EXAMPLES

Figure 1:
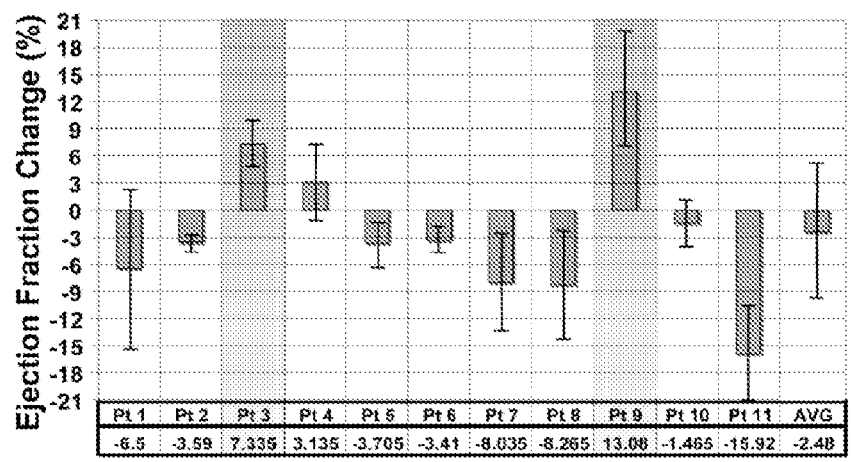
FIG. 1 represents the change of ejection fraction (ΔEF) in %, considered before and after treatment with naïve human mesenchymal stem cells (hMSCs) derived from bone narrow of 11 patients with coronary artery disease.

Patients undergoing coronary artery bypass for ischemic heart disease were randomly selected for bone marrow harvest. They provided informed consent, and study protocols were approved by pertinent Institutional Ethics Committee and Institutional Animal Care and Use Committee. Is worth noting that no injections were made to patients but to mice.

Example 1

Mesenchymal stem cells were derived from human bone marrow withdrawn from the posterior iliac crest of the pelvic bone of 18- to 45-year-old healthy individuals (Cambrex, East Rutherford, N.J.). Based on flow cytometry analysis, the mesenchymal stem cells expressed CD90, CD133, CD105, CD166, CD29, and CD44, and did not express CD14, CD34, and CD45.

Human bone marrow-derived mesenchymal stem cells were cultured in either platelet lysate or serum supplemented with TGFβ-1 (2.5 ng/ml), BMP4 (5 ng/ml), FGF-2 (5 ng/ml), IGF-1 (50 ng/ml), Activin-A (10 ng/ml), Cardiotrophin (1 ng/ml), α-thrombin (1 Unit/ml), and Cardiogenol C (100 nM). After 4-10 days in the platelet lysate-containing culture at a density of about 1000-2000 cells per $cm^2$, the cells were found to express 2-5-fold more MEF2c mRNA, MESP-1 mRNA, Tbx-5 mRNA, GATA6 mRNA, Flk-1 or FOG 1 mRNA than untreated mesenchymal stem cells.

After 5-15 days in the serum-containing culture at a density of about 1000-2000 cells per $cm^2$, the cells were found to express 5-10-fold more MEF2c mRNA, MESP-1 mRNA, Tbx-5 mRNA, GATA 4 mRNA, GATA6 mRNA, Flk-1 or FOG 1 mRNA than untreated mesenchymal stem cells.

The primer pairs used for the RT-PCR analysis were standard primers obtained commercially from Applied Biosystems.

Results demonstrating that the differentiated cardioprogenitor cells have the ability to incorporate into heart tissue as functional cardiomyocytes were obtained both in vivo within the beating heart, and in vitro following autopsy. In vivo, under isoflurane anesthesia, direct myocardial delivery of cardioprogenitor cells into diseased hearts improved cardiac performance as monitored by echocardiography in the short axis with a two-dimensional M-mode probing in the long axis, Doppler pulse wave analysis, and 12-lead electrocardiography.

Harvested heart tissue was fixed in 3% paraformaldehyde, sectioned, and subjected to immuno-probing for human cell tracking. New human derived cardiomyocytes and vasculature, with functional improvement and scar resolution, was documented on analysis in mice treated with cardioprogenitor cells fulfilling release criteria (e.g., elevated level of expression of MEF2c mRNA, MESP-1 mRNA, Tbx-5 mRNA, GATA 4 mRNA, GATA6 mRNA, Flk-1 or FOG 1 mRNA), in contrast to absence of benefit with cells that did not pass the release criteria.

In order to scale-up the production of cardiopoietic cells for autologous injection in patients, an alternative method was considered as immunofluorescence can be time-consuming, qualitative and potentially operator-dependent. One method of choice is real-time quantitative reverse transcription polymerase chain reaction (RT-qPCR). This method gives faster results (within one day) that are operator-independent and quantified relative to a reference standard. In addition, while immunostained samples require one by one fluorescent microscopy evaluation, up to 48 different samples (or conditions) can be tested in duplicate by RT-qPCR using 96-well plates.

In order to identify suitable markers for RT-QPCR, cardiopoietic cells were derived from bone marrow samples obtained from cardiac patients (n=7). Cells were evaluated by immunofluorescence staining for MEF2C and Nkx2.5. RNA was extracted from these cells and expression of Nkx2.5 and MEF2C measured by real-time quantitative PCR.

The reference standard consisted of cells from the same batch not cultured in the presence of the cardiogenic cocktail.

Results were calculated using the double delta-Ct method normalizing the data obtained from treated cells to those from untreated cells.

MEF2C was identified as suitable marker of cardiopoietic cells by both qPCR and immunofluorescence (nuclear translocation) when compared to naive cells. By contrast, the qualitative change in Nkx2.5 seen at the protein level by immunofluorescence (nuclear translocation) was initially not translated into a quantitative change at the RNA level relative to untreated cells. Genes downstream of Nkx2.5 were then investigated, since induction of their expression would depend on nuclear translocation of Nxk2.5. This led to the identification of MESP-1, Flk-1 and Tbx5 as additional suitable genes for identification by QPCR.

Human bone marrow aspirates (15-20 ml) were obtained during coronary artery bypass surgery following sternotomy. Bone marrow was cryostored in a DMSO-based serum-free freezing solution. Mesenchymal stem cells were recruited by platting of raw bone marrow on plastic dishes with a wash at 12 h selecting adhesive cells with identity confirmed by Fluorescence-Activated Cell Sorting (FACS) analysis using the CD34$^-$/CD45$^-$/CD133$^+$ marker panel. Cells were cultured at 37° C. in DMEM supplemented with 5% human platelet lysate (Mayo Clinic Blood Bank, Rochester, Minn.).

Myocardial infarction was performed in nude, immunocompromised mice (Harlan, Indianapolis, Ind.). Following a blinded design, one month post-infarction a total of 600,000 naïve or cardiopoiesis guided hMSC, suspended in 12.5 μl of propagation medium, was injected under microscopic visualization in five epicardial sites on the anterior wall of the left ventricle. Sham underwent the same surgical procedure without cell injection. Myocardial injection of bone marrow hMSC into this chronic infarction model demonstrated heterogeneity in outcome with transplantation of cells from only two out of the eleven studied individuals improving ejection fraction on echocardiography.

Patients 3 and 9 were identified as individuals with a high cardio-generative potential. It was first observed from FIG. 1 that the change of ejection fraction in mice (n=3) treated with hMSC from each patients 3 and 9 was significantly positive, whereas the change for each other patient was not.

Figure 2:
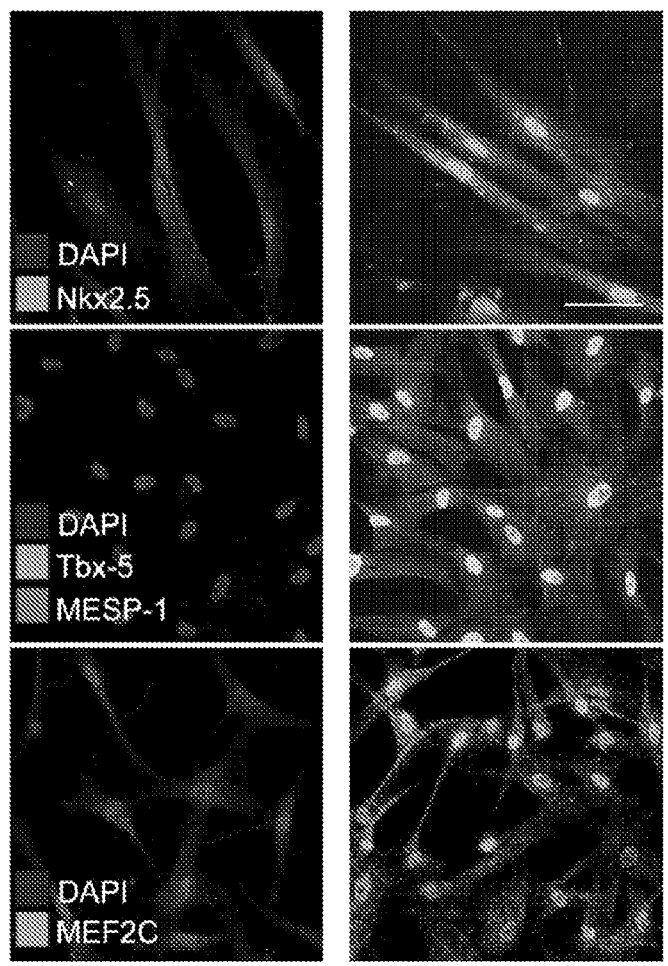
FIG. 2 obtained on confocal microscopy after immunostaining with DAPI, shows protein expression of the cardiac transcription factor content for patient 2 that demonstrated no positive ejection fraction change (left) and for patient 9 (right) that demonstrated a positive ejection fraction change after treatment.

The protein expression of cardiac transcription factors was observed in hMSC on confocal microscopy, as shown in FIG. 2. Bar corresponds to 20 μm representative for all panels.

Immunostaining was performed with antibodies specific for MEF2C (1:400, Cell Signaling Technologies, Danvers, Mass.), Nkx2.5 (1:150, Santa Cruz Biotechnology Inc., Santa Cruz, Calif.), GATA4 (Santa Cruz Biotechnology Inc.), Phospho-AKT$^{Ser473}$ (1:100, Cell Signaling Technologies), Tbx5 (1:5000, Abcam, Cambridge, Mass.), Mesp-1 (1:250, Novus Bio, Littleton, Colo.), Fog-2 (1:100, Santa Cruz Biotechnology), sarcomeric protein α-actinin (1:500, Sigma-Aldrich) and human-specific Troponin-I (1:100, Abcam), mIC2v (1:500, Synaptic Systems, Gottigen, Germany), Sca-1 (1:100, R&D Systems, Minneapolis, Minn.), CD-31/PE-CAM-1 (1:500, Beckman Coulter, Fullerton, Calif.), α-smooth muscle actin (Abcam), human-specific Troponin-I (1:100, Abcam), human Lamin A/C (1:50, Novacastra, New Castle, UK), and Ki67 (1:500, Abcam) following fixation in 3% paraformaldehyde and permeabilization with 1% Triton X-100, and along with DAPI staining to visualize nuclei on confocal microscopy performed with a LSM 510 Laser scanning confocal microscope (Carl Zeiss Inc., Jena, Germany).

Early cardiac transcription factors Nkx2.5, Tbx-5 and MESP1 late cardiac transcription factor MEF2C were observed under staining with DAPI. The results for patient 2 are on the left, the one for patient 9 on the right. The images obtained show that the expression of the cardiac transcription factors is weak for the hMSC from patient 2 and high for the one of patient 9. This corroborates the fact that the hMSC from patient 9 give an efficient therapeutic benefit whereas the hMSC from patient 2 do not. The coloration afforded by DAPI is blue.

On FIG. 2 the first series of images for Nkx2.5 show the nuclei of the cells colored DAPI (left) solely blue for the hMSC of patient 2 (left). A weak green colouration corresponding to the presence of Nkx2.5 in the cytoplasm also appears. The corresponding image for patient 9 (right) shows a higher expression of Nkx2.5 (green) in the cytoplasm and also in the nuclei of the cells.

The second series of images show the cardiac transcription factors Tbx-5 (green) and MESP-1 (red) for patient 2, the nuclei of the cells and coloured in blue by the DAPI, no green or red colour is visible, which corresponds to no expression of TbX-5 and MESP-1. For patient 2, the cytoplasms of the cells are coloured in red and the nuclei in green, which corresponds to strong expression of both cardiac transcription factors and to a translocation of Tbx-5 to the nuclei of the cells.

The third series of images gives results for MEF2C similar to the one for Nkx2.5.

Figure 3:
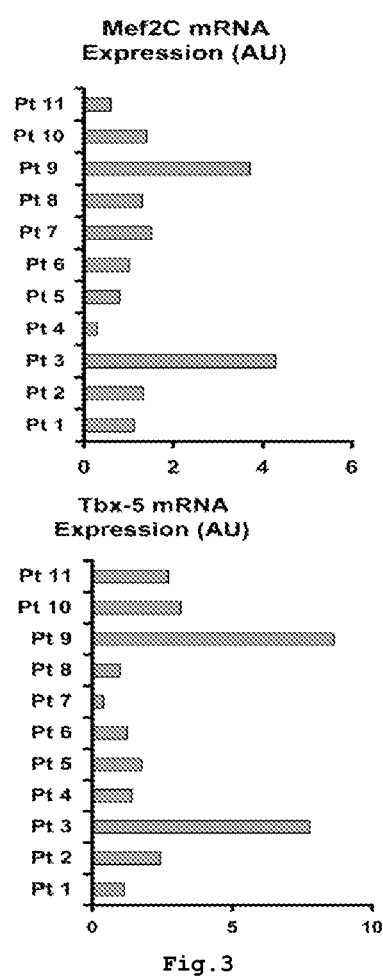
FIG. 3 shows the mRNA expression of two significant cardiac transcription factors mRNA in the hMSCs of the eleven patients.

FIG. 3 shows the mRNA expression studied in qPCR revealing cardiac transcription factor expression (MEF2C and Tbx-5) for the hMSC of the eleven patients of the study.

Quantitative polymerase chain reaction (qPCR) was performed using a TaqMan PCR kit with an Applied Biosystems 7,900HT Sequence Detection System (Applied Biosystems, Foster City, Calif.). TaqMan Gene Expression reactions were incubated in a 96-well plate and run in triplicate. The threshold cycle ($C_T$) was defined as the fractional cycle number at which fluorescence passes a fixed threshold. TaqMan $C_T$ values were converted into relative fold changes determined using the $2^{-\Delta\Delta C_T}$ method, normalized to GAPDH (P/N 435, 2662-0506003) expression.

Genes listed in Table 1, which are representative of cardiac transcriptional activity were evaluated.

Cells were evaluated at the mRNA and protein levels prior to and following a 5-day stimulation with a cardiogenic cocktail comprising human recombinant TGFβ-1 (2.5 ng/ml), BMP4 (5 ng/ml), Cardiotrophin (1 ng/ml), α-thrombin (1 U/ml), and Cardiogenol C (100 nM). Both the MEF2C mRNA and the Tbx-5 mRNA expressions (in arbitrary units AU) are much higher for the hMSC of patients 2 and 9 than for the one of other patients.

Figure 4:
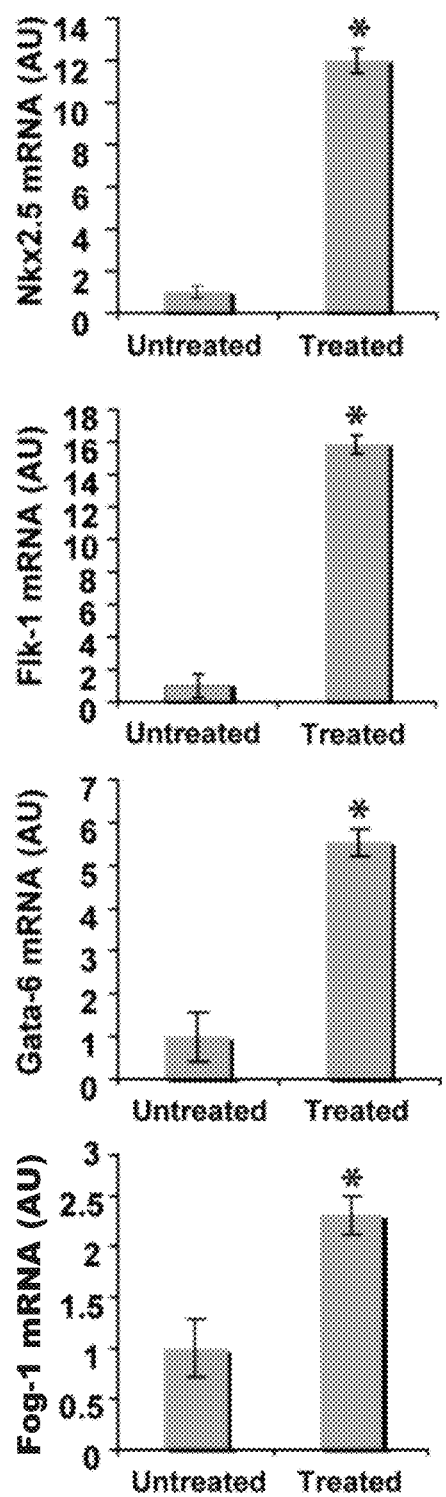
FIG. 4 shows the mRNA expression, in arbitrary units (A.U.) of cardiac transcription factors for respectively Nkx2.5 mRNA, GATA-6 mRNA and Fog-1 mRNA, of untreated, naïve hMSCs (left) and on CP-hMSCs, treated with a cardiogenic cocktail (right).

FIG. 4 shows the mRNA expression, in arbitrary units (A.U.) of cardiac transcription factors for respectively Nkx2.5 mRNA, GATA-6 mRNA and Fog-1 mRNA, of untreated, naïve hMSC (left) and on CP-hMSC, treated with a cardiogenic cocktail (right). It is clear, in each case, that the results are far better when using cells treated with a cardiogenic cocktail.

Figure 5:
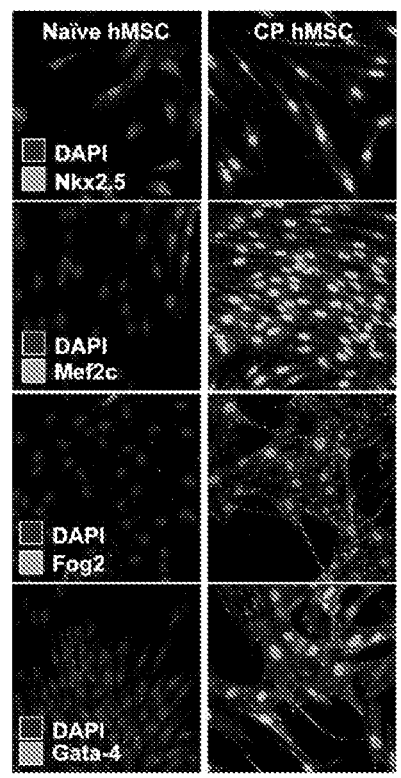
FIG. 5 shows images obtained on confocal microscopy showing nucleartranslocation of Nkx2.5, MEF2C, FOG-2 and GATA4 polypeptides in CP-hMSCs treated with a cardiogenic cocktail (right), compared with naïve hMSCs (left).

FIG. 5 shows images obtained on confocal microscopy showing nuclear translocation Nkx2.5, MEF2c, GATA4 and FOG-2 polypeptides in naïve CP-hMSC treated with a cardiogenic cocktail. Nkx2.5, MEF2c, GATA4 and FOG-2 appear in green and DAPI in blue. On the images of naïve hMSCs, no transcription factor appears. The polypeptides are translocated on the nuclei of CP-hMSCs (right) as indicated by the concentrated green colour.

Figure 6:
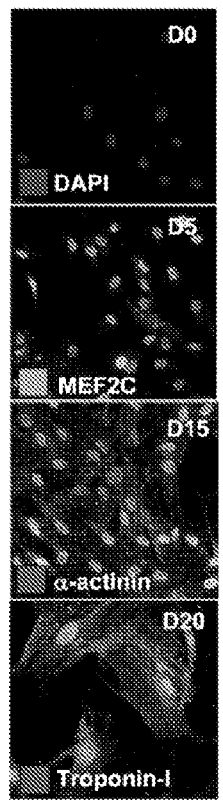
FIG. 6 illustrates the progressive conversion (at days D0, D5, D15, and day D20) from naïve hMSCs to 'cocktail-guided' CP-hMSCs and eventually cardiomyocytes (CM).

FIG. 6 illustrates the progressive conversion (at days D0, D5, D15, and day D20) from naïve hMSCs to 'cocktail-guided' CP-hMSCs and eventually cardiomyocytes, CM. On D0, nuclei are coloured in blue by DAPI. On D5, MEF2C polypeptide is translocated on nuclei (green). On D15, sarcomeric α-actinin is present (red), which shows that sarcomeres are present and hence that the cells are definitively engaged into the cardiomyocytic differentiation and are no longer cardiopoietic. A large quantity of troponin-1 is present in cardiomyocytes on D20 (terminal differentiation).

Figure 7:
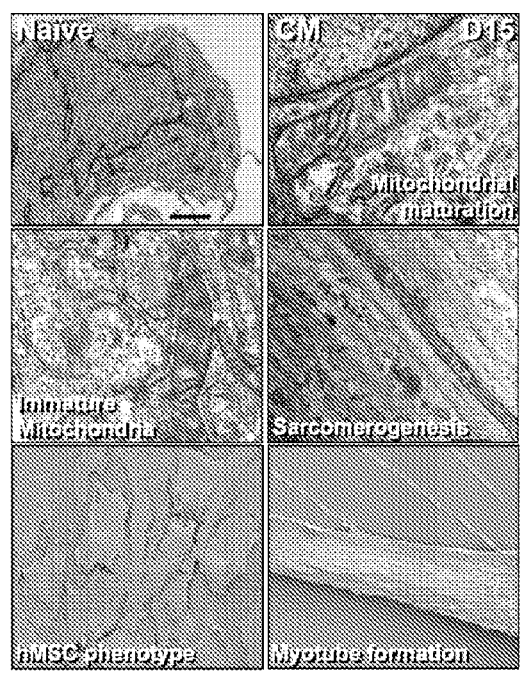
FIG. 7 shows the transition electron microscopy ultrastructure of naïve hMSC and cocktail-guided cardiomyocyte.

FIG. 7 shows the transition electron microscopy ultrastructure of naïve hMSC (left) and cocktail-guided cardiomyocyte (right). To this end, cells were cultured in 1% platelet lysate for 15 days The cardiomyocytes present a mitochondrial maturation, a sarcomerogenesis and formation of myotubes.

Figure 8:
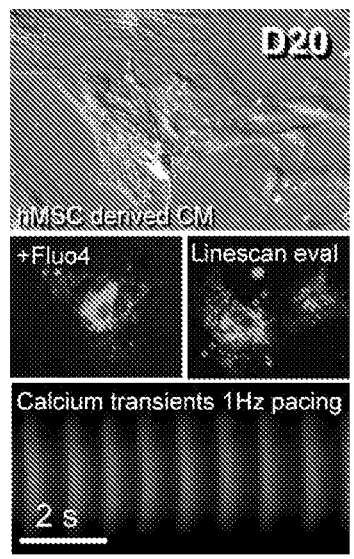
FIG. 8 shows a cocktail-guided cardiomyocyte in light microscopy.

FIG. 8 shows a cocktail-guided cardiomyocyte in light microscopy. Maturation of the excitation-contraction system was assessed through induction of calcium transients.

To this end, cells were cultured for 15 days following 5 days of cocktail stimulation and loaded for 30 min at 37° C.

TABLE 1

| Applied Biosystems Assay ID | Gene name | Gene symbol |
| --- | --- | --- |
| Hs00231763_m1 | Homeobox transcription factor or NK2 transcription factor related, locus 5 | Nkx2.5 or NKX2-5 or NKX2.5 |
| Hs00171403_m1 | zinc finger cardiac transcription factor or GATA binding protein 4 | GATA-4 or, GATA4 (AB) |
| Hs00231149_m1 | myocyte enhancer factor 2C | MEF2c or MEF2C |
| Hs00361155_m1 | T-box transcription factor or T-box 5 | Tbx5 or TBX5 |
| Hs00542350_m1 | GATA co-factor ("Friend of GATA") or zinc finger protein, multitype 1 | FOG 1 of FOG-1 or FOG1 |
| Hs00251489_m1 | Helix-loop-helix transcription factor mesoderm posterior 1 homolog (mouse) (AB) | Mesp1 or MESP1 |
| Hs00232018_m1 | GATA binding protein 6 (AB) | GATA-6 or GATA6 |
| Hs00911699_m1 | Kinase insert domain receptor (a type III receptor tyrosine kinase) | Flk-1, or FLK1 or KDR |

Left ventricular function and structure were serially followed by transthoracic echocardiography (Sequoia 512; Siemens, Malvern, Pa. and VisualSonics Inc, Toronto, Canada). Ejection fraction (%) was calculated as [(LVVd-LVVs)/LVVd]×100, where LVVd is left ventricular end-diastolic volume (μl), and LVVs is left ventricular end-systolic volume (μl).

with 5 μM of the calcium-selective probe fluo-4-acetoxymethyl ester (Molecular Probes, Carlsbad, Calif.) for live imaging using a temperature controlled Zeiss LSM 510 microscope (Zeiss) and line-scan images acquired during 1 Hz stimulation.

Figure 9:
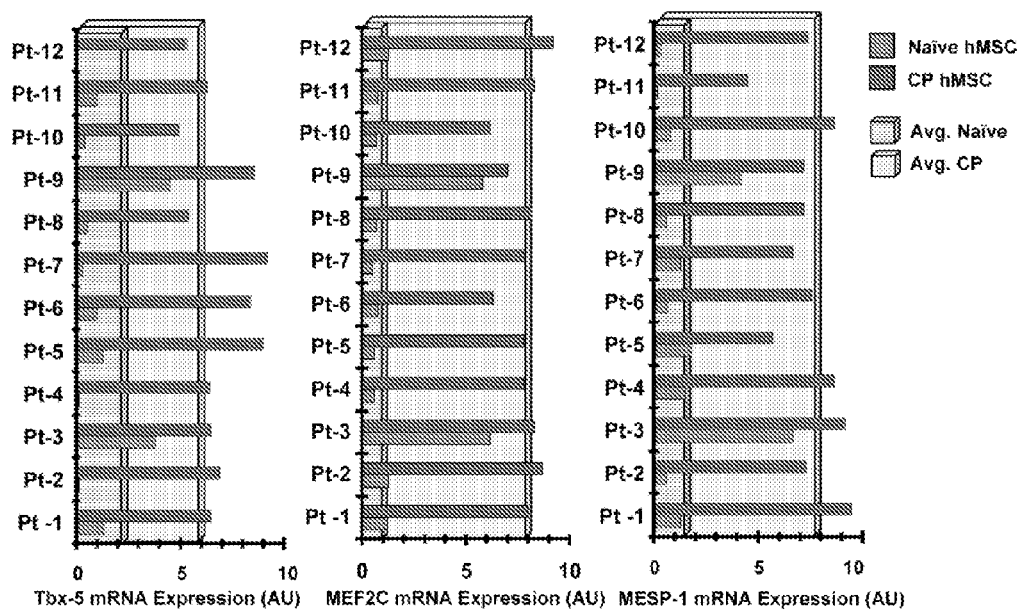
FIG. 9 represents, on the first graph on the left, the Tbx-5 mRNA expression (in AU) for naïve hMSC and CP-hMSC from each patient of FIG. 1, the results for the naïve cells being on the right and the one for the CP cells being on the left of the histogram. The second graph in the middle presents MEF2C mRNA expression, and the third graph on the right presents MESP-1 mRNA expression. The average values for the naïve cells from all patients and the one for the CP cells for all patients are given in the background of the histogram.

FIG. 9 shows a 3-, 8-, and 8-fold increase in Tbx-5, MEF2C and MESP-1 in treated versus untreated hMSC.

Figure 10:
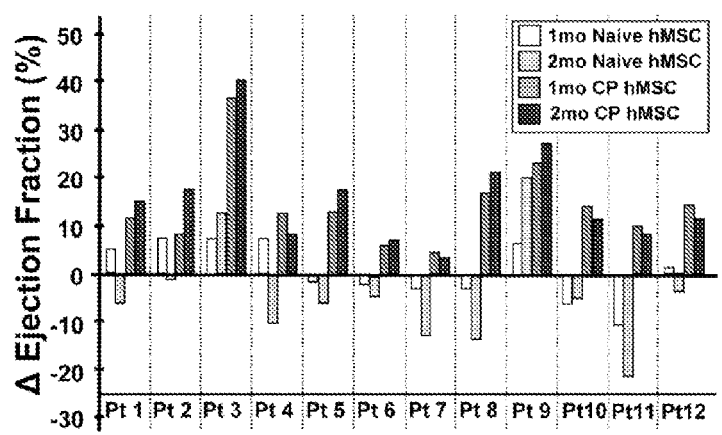
FIG. 10 is a graph which represents the ejection fraction change (ΔEjection Fraction) after treatment of heart with different quantities of naïve hMSC (right part of histogram for each of twelve patients) versus treatment of hearts with CP-hMSCs, i.e. cocktail-guided hMSC (CP-hMSC).

As shown in FIG. 10, CP-hMSCs meeting CARPI criteria, were delivered in vivo one-month following infarction and significantly improved ejection fraction over naïve patient-matched hMSC.

Figure 11:
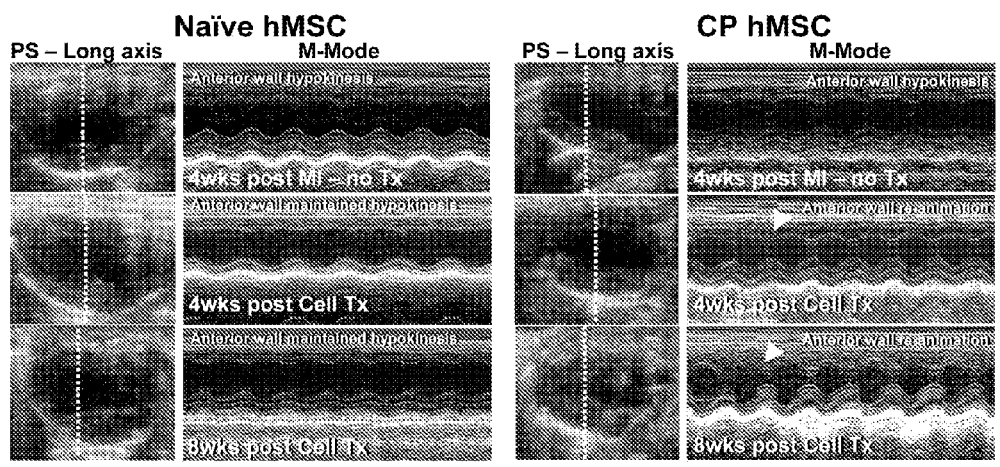
FIG. 11 represents the echocardiography of infarcted hearts untreated (left) and treated with cardiopoietic cells (right), which shows a far better anterior wall reanimation upon treatment with CP-hMSCs.

FIG. 11 represents an echocardiography of infarcted hearts untreated (left) and treated with cardiopoietic cells (right), which shows a far better anterior wall reanimation upon treatment with CP-hMSCs. Electrocardiograms were recorded using four-limb-lead electrocardiography (MP150; Biopac, Goleta, Calif.) under light anaesthesia (1.5% isoflurane).

On echocardiography, contractility improved by 15% and 20% at one- and two-months, respectively, following treatment with CP-hMSC (n=14), in contrast to marginal change recorded with naïve hMSC (n=17) or sham (n=10; FIG. 9). On top: Echocardiography of infarcted hearts 4 weeks following coronary ligation and 1 day prior to cellular transplant (4 wks post MI—no Tx) revealed on M-Mode an akinetic anterior wall in both study groups. Middle: 4 weeks after cellular transplantation (4 wks post Cell Tx), naïve hMSC treated hearts demonstrated maintained akinesis in the anterior wall, in contrast to re-animation in the CP-hMSCs treated group. Lower: 8 weeks following cellular transplantation (8 wks post Cell Tx), naïve hMSC treated hearts continued to show limited evidence for myocardial repair versus robust contractile activity in the CP hMSC treated infarcted hearts. Left panels represent para-sternal (PS) long axis views, with dash line indicating level of 2-D M-Mode capture. Arrowheads in right panels indicate anterior wall re-animation.

Figure 12:
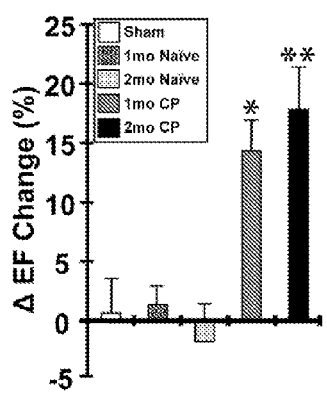
FIG. 12 is a graph similar to FIG. 5 showing the ejection fraction change (ΔEF) after injection of naïve (on the left) and cardiopoietic cells (on the right) into infracted myocardium. Sham is injection without cells.

FIG. 12 shows that on average, guided cardiopoietic hMSC achieved a marked improvement at the one and two month follow-up following injection into infarcted myocardium. In contrast, naïve hMSC or sham controls had limited impact on ejection fraction. Star and double star indicate a p<0.01 over naïve hMSC for the two time points.

Figure 13:
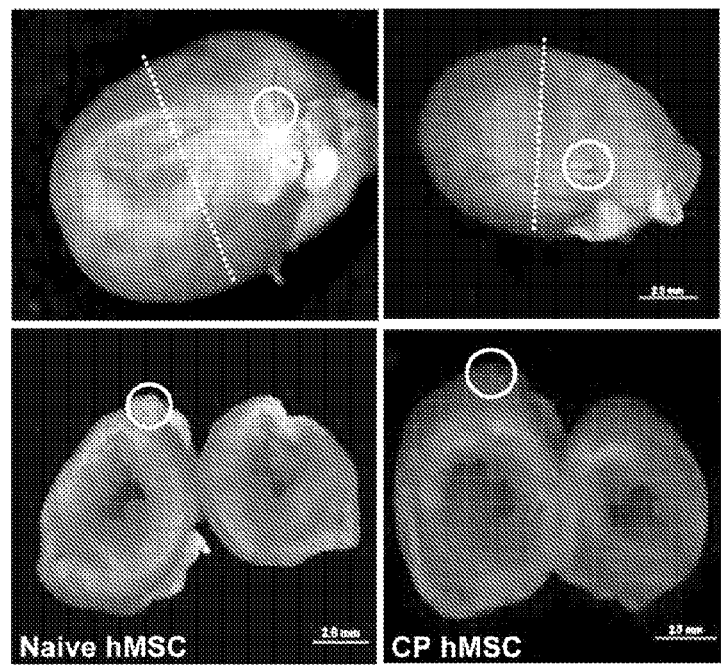
FIG. 13 shows murine infarcted hearts treated with naïve hMSC and CP-hMSCs six months following treatment initiation. Aneurysms and scar, which remained uncorrected in naïve hMSCs treated hearts, were resolved with CP-hMSCs treatment that induced re-muscularization.

In hearts treated with cardiopoietic cells derived from hMSC, functional improvement correlated on three-month and 18-month histopathological evaluation with myocardial regeneration. Aneurysms and scar, which remained uncorrected in naïve hMSC-treated hearts, were resolved with cardiopoietic hMSC treatment that induced re-muscularization (FIG. 13).

Gross pathological evaluation demonstrated resolution of scar downstream of left anterior descending (LAD) artery ligation (yellow circle on the hearts) with, on cross-section, robust re-muscularization and diminished remodeling in cardiopoietic (CP, right) in contrast to naïve (left) hMSC-treated infarcted hearts at 6-months following treatment initiation. These results are particularly good.

Probing for ALU-DNA was performed using human ALU-Probe (Biogenex, San Ramon, Calif.) by hybridization at 85° C. for 5-10 minutes and incubation at 37° C. overnight followed by anti-Fluorescein GFP-labeled secondary detection.

Figure 14:
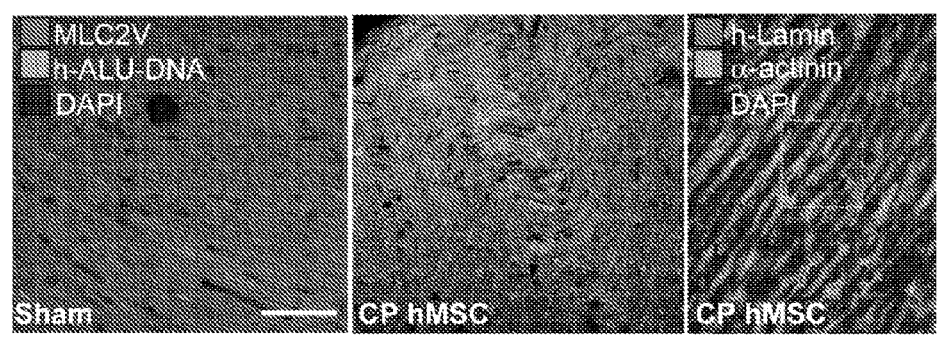
FIG. 14 shows that confocal resolution revealed, in the cardiopoietic hMSC treated murine myocardium, widespread presence of human-derived cells with positive staining for h-ALU-DNA sequences specific to the human species validated with human-specific lamin immunostaining, all of which were absent in infarcted controls.

Confocal resolution revealed, in the CP-hMSC-treated murine myocardium, widespread presence of human-derived cells with positive staining for ALU DNA sequences specific to the human species validated with human-specific lamin immunostaining, all absent in infarcted controls (FIG. 14).

In contrast to sham (left), cardiopoietic hMSC treated hearts on confocal microscopy evaluation revealed dramatic presence of human nuclei as stained by a human h-ALU DNA probe (middle) imbedded within the murine infarcted myocardium, further confirmed with additional staining for a human-specific lamin antibody (right, inset shown in FIG. 14). Frozen myocardial sections were made from super-oxygenated 3% paraformaldehyde in PBS perfusion fixed hearts. Bar indicates 50 μm.

Figure 15:
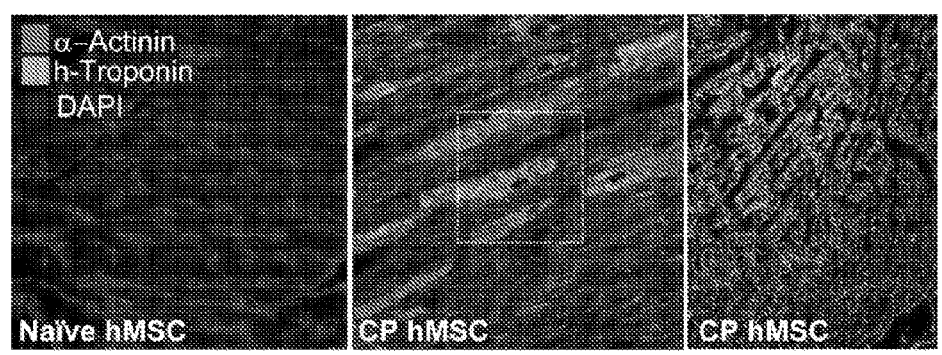
FIG. 15 shows that cardiomyocytes of human origin were tracked by co-localization of human cardiac troponin-I and α-actinin in cardiopoietic hMSC-treated hearts. Cardiomyocytes of human origin were absent from naïve hMSC-treated hearts. Quantification within infarcted anterior walls revealed 3±2% and 25±5% of myocardial nuclei in naïve versus CP-hMSC-treated hearts, implying enhanced engraftment with cardiopoietic hMSC treatment.

FIG. 15 shows that human-specific troponin-I antibody revealed no staining in naïve (left) versus significant staining in the anterior wall of cardiopoietic hMSC treated hearts (middle and right panels)

Figure 16:
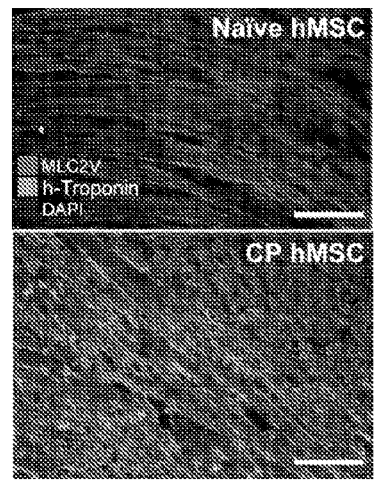
FIG. 16 contains photographs of naïve and CP hMSC stained for human troponin, ventricular myosin light chain mIC2V, and DAPI. Ventricular cell phenotype was corroborated with counter staining of human-troponin positive cells with ventricular myosin light chain mIC2V immunostaining in repaired anterior wall, as shown in FIG. 15 or resolving scar as shown in FIG. 17.

Moreover, as shown in FIG. 16 human troponin-I staining of naïve (top) versus cardiopoietic (bottom) hMSC treated hearts, counterstained with mIC2v, demonstrated generation of ventricular myocardium from engrafted human cells. Bars indicate 20 μm (top) and 50 μm (bottom).

Figure 17:
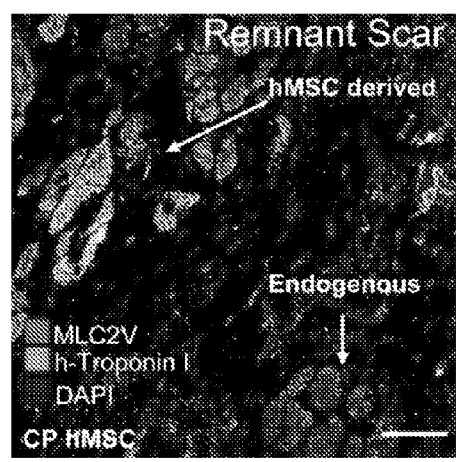
FIG. 17 is a photograph of a remnant scar stained for human troponin, ventricular myosin light chain mIC2V, and DAPI.

As illustrated in FIG. 17 within the remnant scar of cardiopoietic derived from hMSC-treated hearts, human stem cell derived myocardium could be distinguished from native murine myocardium with human troponin colocalization with mIC2V. Bar indicates 50 μm.

Figure 18:
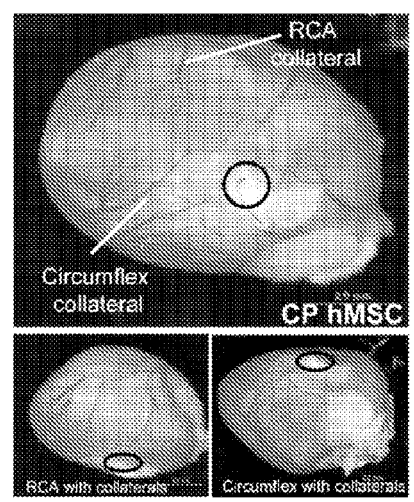
FIG. 18 contains photographs of CP-hMSCs-treated regenerating myocardium demonstrating angiogenesis distal to the occluded coronary vessel.

In FIG. 18 surface microscopy detected angiogenesis distal to the ligated LAD (black circle) in CP-hMSCs-treated hearts arising from the right coronary artery (RCA; left bottom) and circumflex (right bottom).

Figure 19:
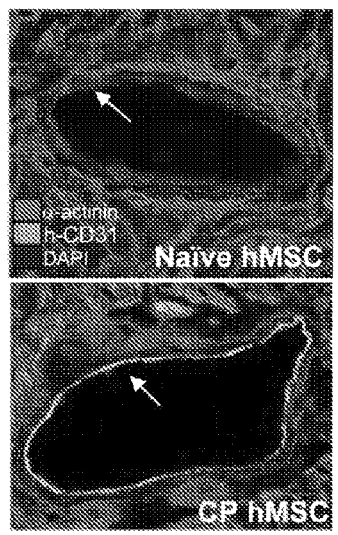
FIG. 19 demonstrates CP-hMSCs contribution to neo-vascularization via expression of human PECAM-1 (CD-31) within the myocardial vasculature.

FIG. 19 shows confocal evaluation of collateral vessels from cardiopoietic hMSC treated hearts demonstrated human-specific CD-31 (PECAM-1) staining. Bar represents 20 μm.

Figure 20:
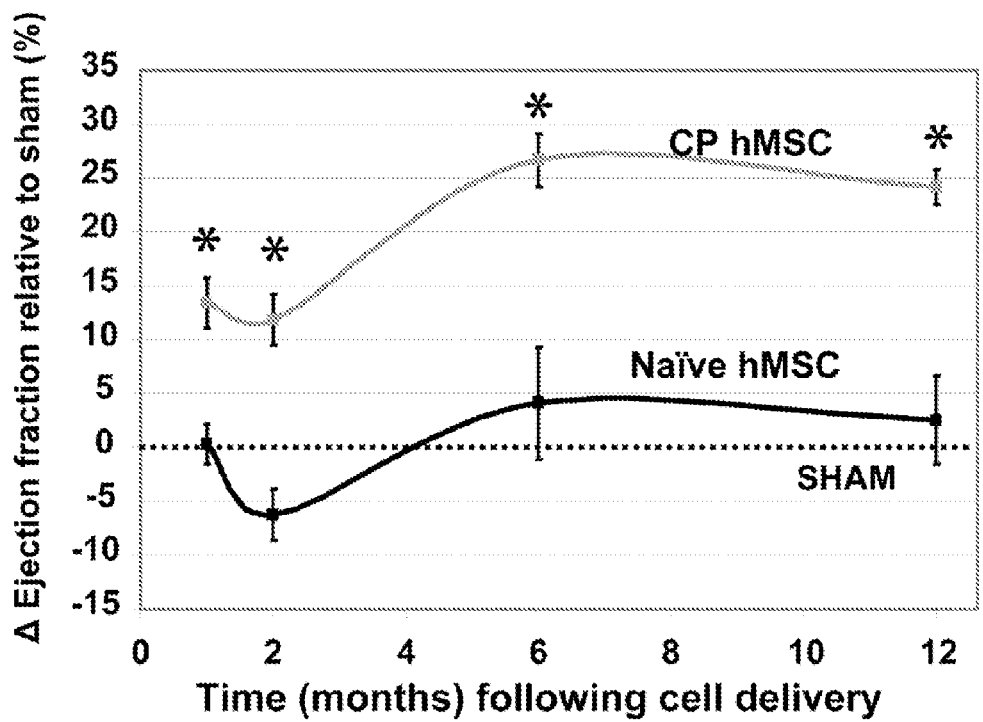
FIG. 20 is a graph plotting Δ ejection fraction relative to sham (%) versus time (months) following cell delivery. The long-term impact of CP-hMSCs treatment was tracked for more than one 1-year, or one third of murine lifespan which would translate into 25-years of human life. Relative to sham, treatment with naïve hMSC showed a 5% and 2.5% ejection fraction effect at 6 and 12 months, respectively. In contrast, cardiopoietic hMSC treated infarcted mice demonstrated significant ejection fraction improvement of 25% at 6 and 12 months relative to sham.
Figure 21:
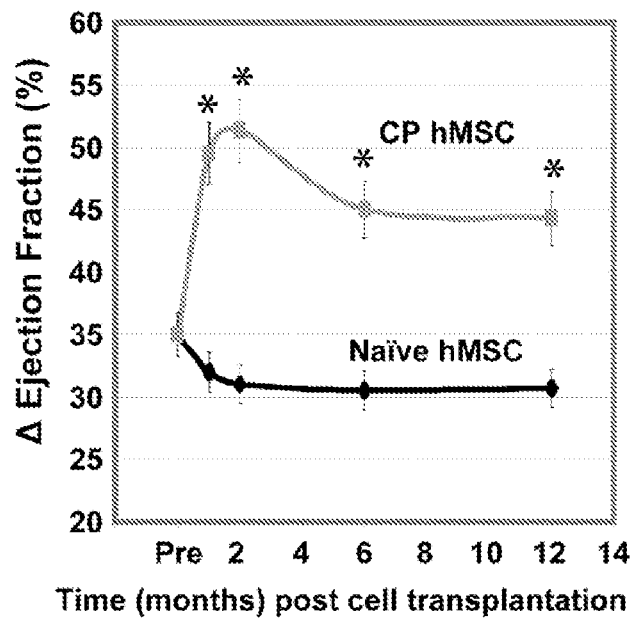
FIG. 21 is a graph plotting Δ ejection fraction (%) versus time (months) post cell transplantation. The infarcted cohort was stratified to evaluate efficacy in subgroups with documented overt heart failure (ejection fraction<45%) at the time of intervention. Despite equivalent pre-treatment ejection fraction at 35%, only cardiopoietic hMSC treatment improved absolute ejection fraction by 10% at 6 and 12-months, in contrast to a 5% decline in ejection fraction in the naïve hMSC-treated cohort.

FIG. 20 shows the evolution of the change of ejection fraction relative to sham in %, during 12 months, for treatment with both naïve and cocktail-guided (CP) hMSC. Relative to sham, treatment with naïve hMSC showed a 5% and 2.5% ejection fraction effect at 6 and 12 months, respectively.

Figure 22:
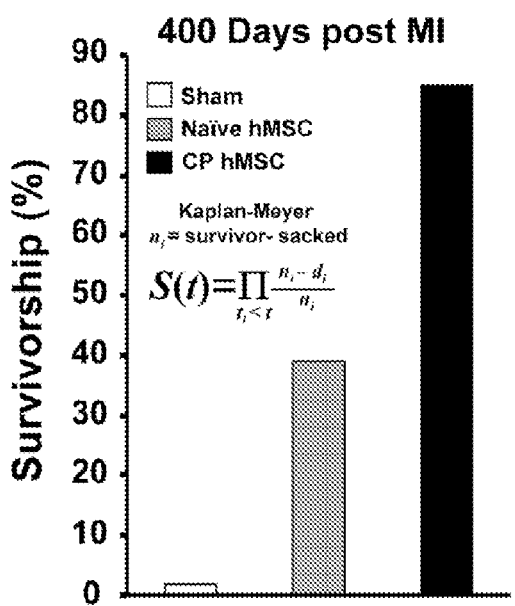
FIG. 22 is a bar graph plotting survivorship (%) for the indicated subgroups of mice. In overt heart failure subgroups at 400 days follow-up, no survivors were present in the sham and mortality of >50% was recorded with naïve hMSC treatment. In contrast, a >80% survival was attained with cardiopoietic hMSC treatment.
Figure 23:
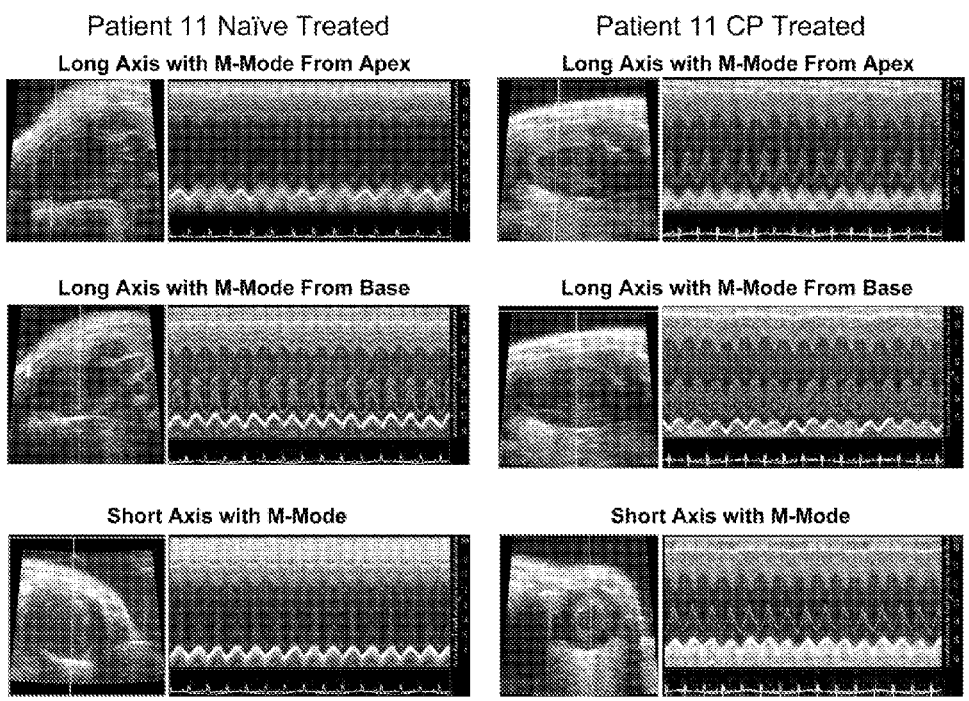
FIG. 23 illustrates the safety of treatment with CP-hMSCs, determined by pathological examination and electrocardiography.

In contrast, CP-hMSCs-treated infarcted mice demonstrated significant ejection fraction improvement of 25% at 6 and 12 months relative to sham (FIG. 20). Furthermore, the infarcted cohort was stratified to evaluate efficacy in subgroups with documented overt heart failure (ejection fraction<45%) at the time of intervention. Despite equivalent pre-treatment ejection fraction at 35%, only cardiopoietic hMSC treatment improved absolute ejection fraction by 10% at 6 and 12-months, in contrast to a 5% decline in ejection fraction in the naïve hMSC-treated cohort (FIG. 23). As shown in FIG. 22, superior survival benefit in the cardiopoietic hMSC treated group in contrast to naïve treated cohort and sham was determined through application of the Kaplan-Meier function with censoring.

Efficacy of cardiopoietic (CP) hMSC was demonstrated by echocardiography at 1-year follow-up (see FIG. 25). Long axis imaging of naïve stem cell treated hearts revealed a fibrotic and hypokinetic anterior wall most evident on apical M-Mode evaluation (Patient 11, left panels). In contrast, CP-hMSC-treated hearts revealed a robust contractile profile throughout the anterior wall reflecting a sustained benefit from guided stem cell therapy (Patient 11, right panels).

Example 2

Similar results have been observed by treating stem cells with a cocktail containing recombinant TGFβ-1 (2.5 ng/ml), BMP4 (5 ng/ml), C ardiotrophin (1 ng/ml), Cardiogenol C (100 nM) and α-thrombin, (1 U/ml), FGF-2 (10 ng/ml), IGF-1 (50 ng/ml) and Activin-A (5 ng/ml) used in a combinatorial fashion.

Example 3

Similar results have been observed by treating stem cells with a cocktail containing recombinant TGF-β1 (2.5 ng/ml), BMP-4 (5 ng/ml), Activin-A (5 ng/ml), FGF-2 (10 ng/ml), IL-6 (100 ng/ml), Factor IIa (hα-thrombin, 1 U/ml), IGF-1 (50 ng/ml), and retinoic acid (1 μM) used in a combinatorial fashion.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for increasing expression of Nkx2.5 mRNA, GATA 6 mRNA, and Fog 1 mRNA within human mesenchymal stem cells, wherein said method comprises culturing human mesenchymal stem cells in the presence of a composition comprising TGFβ-1, BMP4, α-thrombin, Cardiotrophin, and Cardiogenol C.

2. The method of claim 1, wherein said composition comprises between 1 and 5 ng of said TGFβ-1 per ml, between 1 and 10 ng of said BMP4 per ml, between 0.5 and 5 ng of said Cardiotrophin per ml, between 0.5 and 5 units of said α-thrombin per ml, and between 50 and 500 nM of said Cardiogenol C.

3. The method of claim 1, wherein said composition comprises 2.5 ng/ml of recombinant TGFβ-1, 5 ng/ml of BMP4, 1 ng/ml of Cardiotrophin, and 100 nM of Cardiogenol C.

4. The method of claim 1, wherein said mesenchymal stem cells express CD90, CD105, CD133, CD166, CD29, and CD44 on the cell surface and do not express CD14, CD34, and CD45 on the cell surface.

5. The method of claim 1, wherein said composition is comprised in a medium selected from the group consisting of media containing fetal calf serum, media containing human serum, media containing platelet lysate, and media containing mixtures thereof.

* * * * *